(12) United States Patent
Rawas-Qalaji et al.

(10) Patent No.: US 9,877,921 B2
(45) Date of Patent: Jan. 30, 2018

(54) EPINEPHRINE NANOPARTICLES, METHODS OF FABRICATION THEREOF, AND METHODS FOR USE THEREOF FOR TREATMENT OF CONDITIONS RESPONSIVE TO EPINEPHRINE

(71) Applicant: NOVA SOUTHEASTERN UNIVERSITY, Fort Lauderdale, FL (US)

(72) Inventors: Mutasem Rawas-Qalaji, Fort Lauderdale, FL (US); Ousama Rachid, Winnipeg (CA); Keith Simons, Winnipeg (CA); Estelle Simons, Winnipeg (CA)

(73) Assignee: NOVA SOUTHEASTERN UNIVERSITY, Fort Lauderdale, FL (US)

( * ) Notice: Subject to any disclaimer, the term of this patent is extended or adjusted under 35 U.S.C. 154(b) by 0 days.

(21) Appl. No.: 15/266,843

(22) Filed: Sep. 15, 2016

(65) Prior Publication Data

US 2017/0000735 A1    Jan. 5, 2017

Related U.S. Application Data

(63) Continuation of application No. 14/353,118, filed as application No. PCT/US2012/061074 on Oct. 19, 2012, now abandoned.

(60) Provisional application No. 61/550,359, filed on Oct. 21, 2011.

(51) Int. Cl.
| | |
|---|---|
| *A61K 9/16* | (2006.01) |
| *A61K 9/14* | (2006.01) |
| *A61K 9/00* | (2006.01) |
| *A61K 31/137* | (2006.01) |
| *A61K 47/36* | (2006.01) |
| *A61K 47/02* | (2006.01) |

(52) U.S. Cl.
CPC ............ *A61K 9/14* (2013.01); *A61K 9/006* (2013.01); *A61K 31/137* (2013.01); *A61K 47/02* (2013.01); *A61K 47/36* (2013.01)

(58) Field of Classification Search
CPC . A61K 9/14; A61K 9/141; A61K 9/16; A61K 9/51; A61K 9/5107; A61K 9/5161; A61K 9/5192

See application file for complete search history.

(56) References Cited

U.S. PATENT DOCUMENTS

| | | | |
|---|---|---|---|
| 5,143,731 A * | 9/1992 | Viegas | A61K 9/0014 424/430 |
| 5,223,614 A | 6/1993 | Schromm et al. | |
| 5,567,439 A | 10/1996 | Myers et al. | |
| 5,587,172 A | 12/1996 | Cherukuri et al. | |
| 5,622,716 A | 4/1997 | Barth | |
| 5,622,717 A | 4/1997 | Fuisz | |
| 5,654,003 A | 8/1997 | Fuisz et al. | |
| 5,871,781 A | 2/1999 | Myers et al. | |
| 6,024,981 A | 2/2000 | Khankari et al. | |
| 6,221,392 B1 | 4/2001 | Khankari et al. | |
| 6,264,981 B1 | 7/2001 | Zhang et al. | |
| 6,309,663 B1 | 10/2001 | Patel et al. | |
| 6,368,625 B1 | 4/2002 | Siebert et al. | |
| 6,833,377 B2 | 12/2004 | Serdyuk | |
| 2003/0021841 A1 | 1/2003 | Matharu et al. | |
| 2003/0216413 A1 | 11/2003 | Root-Bernstein et al. | |
| 2004/0076588 A1 | 4/2004 | Batycky et al. | |
| 2004/0234611 A1 | 11/2004 | Ahlheim et al. | |
| 2005/0130935 A1 | 6/2005 | Weidner | |
| 2006/0093677 A1 | 5/2006 | Chickering et al. | |
| 2007/0059361 A1 | 3/2007 | Rawas-Qalaji et al. | |
| 2007/0092553 A1 | 4/2007 | Tengler et al. | |
| 2007/0154549 A1 | 7/2007 | Morton et al. | |
| 2007/0202163 A1 | 8/2007 | Rawas-Qalaji et al. | |
| 2007/0293580 A1 | 12/2007 | Hill | |
| 2008/0032934 A1 * | 2/2008 | Ellis-Behnke | A61L 15/42 514/9.4 |
| 2008/0069779 A1 | 3/2008 | Tamarkin et al. | |

(Continued)

FOREIGN PATENT DOCUMENTS

| | | |
|---|---|---|
| CN | 101669917 A | 3/2010 |
| EP | 0159237 A1 | 10/1985 |

(Continued)

OTHER PUBLICATIONS

Abdelbary et al., "Determination of the in Vitro Disintegration Profile of Rapidly Disintegrating Tablets and Correlation with Oral Disintegration," Int. J. Pharm., 292:29-41(2005).
"Adrenaline into Melanin," Br. Med J., 2:486 (1971).
Allen, "Rapid-Dissolve Technology: An Interview with Lloyd V. Allen, Jr. PhD, RPh," Int. J. Pharm. Compound., 7:449-450 (2003).
Aly et al., "Superdisintegants for Solid Dispersion to Produce Rapidly Disintegrating Tenoxicam Tablets via Camphor Sublimation," Pharm. Tech., 7:68-78 (2005).
Aurora et al., "Oral Disintegrating Dosage Forms: An Overview," Drug Deliv. Technol., 5:50-54 (2005).

(Continued)

*Primary Examiner* — Micah Paul Young
(74) *Attorney, Agent, or Firm* — Fleit Gibbons Gutman Bongini & Bianco PL; Paul D. Bianco; Katharine Davis Wong

(57) ABSTRACT

The invention provides compositions including epinephrine nanoparticles and methods for therapeutic use of the compositions in the treatment of conditions responsive to epinephrine such as a cardiac event or an allergic reaction, particularly anaphylaxis. The epinephrine nanoparticles can be incorporated into orally-disintegrating and fast-disintegrating tablet pharmaceutical formulations and can significantly increase the sublingual bioavailability of epinephrine, and thereby reduce the epinephrine dose required. Additionally, the invention provides methods for fabrication of stabilized epinephrine nanoparticles for use in the described compositions.

19 Claims, 11 Drawing Sheets

(56) References Cited

U.S. PATENT DOCUMENTS

| | | |
|---|---|---|
| 2009/0263476 A1 | 10/2009 | Jobodevairkkam et al. |
| 2010/0035800 A1 | 2/2010 | Desai et al. |
| 2011/0182805 A1* | 7/2011 | DeSimone ............ A61K 9/0097 424/1.11 |
| 2011/0223203 A1 | 9/2011 | Berkland et al. |
| 2012/0322884 A1 | 12/2012 | Rawas-Qalaji et al. |
| 2014/0242177 A1 | 8/2014 | Rawas-Qalaji et al. |
| 2015/0164827 A1 | 6/2015 | Rawas-Qalaji et al. |
| 2016/0374966 A1 | 12/2016 | Rawas-Qalaji et al. |

FOREIGN PATENT DOCUMENTS

| | | |
|---|---|---|
| WO | WO 1994/009762 A1 | 5/1994 |
| WO | WO 2014/153559 A1 | 9/2014 |

OTHER PUBLICATIONS

Bi et al., "Evaluation of Rapidly Disintegrating Tablets Prepared by a Direct Compression Method," Drug Dev. Ind. Pharm., 25:571-581 (1999).
Bi et al., "Preparation and Evaluation of a Compressed Tablet Rapid Disintegration in the Oral Cavity," Chem. Pharm. Bull., 44:2121-2127 (1996).
Birudaraj et al., "Buccal Permeation of Bispirone: Mechanistic Studies on Transport Pathways," J. Pharm. Sci., 94:70-78 (2004).
Chang et al., "Fast Dissolving Tablets," Pharm. Tech., 24:52-58 (2000).
Connors et al. In Chemical Stability of Pharmaceuticals: A Handbook for Pharmacists, Wiley-Interscience Publication: New York (1986).
Cunningham et al., "Comparative Pharmacokinetics of Oral Versus Sublingual Clonidine," J. Clin. Anesth., 6:430-433 (1994).
De Vries et al., "Developments in Buccal Drug Delivery," Crit. Rev. Ther. Drug Carr. Syst., 8:271-303 (1991).
Dobetti, "Fast-Melting Tablets: Developments and Technologies," PharmTech. Eur., 12:32-42 (2000).
Dor et al., "In Vitro Determination of Disintegration Time of Quick-Dissolve Tablets Using a New Method," Pharm. Dev. Technol., 5:575-577 (2000).
El-Arini et al., "Evaluation of Disintegration Testing of Different Fast Dissolving Tablets Using the Texture Analyser," Pharm. Dev. Technol., 7:361-371 (2002).
Fell et al., "Determination of Tablet Strength by the Diametral Compression Test," J. Pharm. Sci., 59:688-691 (1970).
Ganhao et al., "Evaluation of a Single Plasma Catecholamino Extraction Procedure Prior to High-Performance Liquid Chromatography and Electrochemical Detection," J. Chromatogr., 564:55-66 (1991).
Gu et al., "Is Epinephrine Administration by Sublingual Tablet Feasible for the First-Aid Treatment of Anaphylaxis? A Proof of Concept Study," Biopharm. Drug Dispos., 23:213-216 (2002).
Gu et al., "Epinephrine Absorption After Different Routes of Administration in an Animal Model," Biopharm. Drug Dispos., 20:401-405 (1999).
Hamilton et al., "Advanced Orally Disintegrating Tablets Bring Significant Benefits to Patients and Product Life Cycles," Drug Deliv. Technol., 5:34-37 (2005).
Hedenus et al., "Characterization of Instantaneous Water Absorption Properties of Pharmaceutical Excipients," Int. J. Pharm., 141:141-149 (2000).
Hjemdahl, "Catecholamine Measurements in Plasma by High-Performance Liquid Chromatography With Electrochemical Detection," Methods Enzymol., 142:521-534 (1987).
Hjemdahl, "Inter-Laboratory Comparison of Plasma Catecholamine Determinations Using Several Different Assays," Acta Physiol. Scand. Suppl., 527:43-54 (1984).
"Human Physiology: From Cells to Systems," Sherwood ed.; Brooks/Cole/Thomson Learning: Belmont, CA, 2004; Chapter 16, pp. 591-645.

Ishikawa et al., "Pharmacokinetics of Acetaminophen From Rapidly Disintegrating Compressed Tablet Prepared Using Microcrystalline Cellulose (PH-M-06) and Spherical Sugar Granules," Chem. Pharm. Bull., 49:230-232 (2001).
Ishikawa et al., "Preparation of Rapidly Disintegrating Tablet Using New Types of Microcrystalline Cellulose (PH-M Series) and Low Substituted-Hydroxypropylcellulose or Spherical Sugar Granule by Direct Compression Method," Chem. Pharm. Bull., 49:134-139 (2001).
Kroboth et al., "Triazopam Pharmalinetics After Intravenous, Oral, and Sublingual Administration," J. Clin. Psychopharmacol., 15:259-262 (1995).
Lieberman et al., "Joint Task Force on Practice Parameters," J. Allergy Clin. Immunol., 115:S483-S523 (2005).
Lieberman et al., "Use of Epinephrine in the Treatment of Anaphylaxis," Curr. Opin. Allergy Clin. Immunol., 3:313-318 (2003).
Mitra et al., "Peptides and Proteins—Buccal Absorption," Encyclopedia of Pharm. Tech., pp. 2081-2095 (2002).
Motwani and Lipworth, "Clinical Pharmacokinetics of Drugs Administered Buccaly and Sublingually," Clin. Pharmacokinet., 21:83-94 (1991).
Parakh et al., "A Review of Mouth Dissolving Tablet Technologies," Pharm. Tech. 27:92-100 (2003).
Physical Tests: Dissolution (711); 22/17 ed., Rockville, MD: United States Pharmaceutical Convention Inc., 2007.
Price et al., "Single-Dose Pharmacokinetics of Sublingual Versus Oral Administration of Micronized 17β-Estradiol," Obstet. Gynecol., 89:340-345 (1997).
Rachid et al., "An Electronic Tongue: Evaluation of the Masking Efficacy of Sweetening and/or Flavoring Agents on the Bitter Taste of Epinephrine," AAPS PharmSciTech, 11:550-557 (2010).
Rachid et al., "Dissolution Testing of Sublingual Tablets: a Novel in Vitro Method," AAPS PharmSciTech, 12:544-552 (2011).
Rawas-Qalaji et al., "Fast-Disintegrating Sublingual Epinephrine Tablets: Effect of Drug and Tablet Dimensions on Tablet Characteristics," AAPS 7(52): Abstract W5220 (2005).
Rawas-Qalaji et al., "Sublingual Epinephrine Tablets Versus Intramuscular Injection of Epinephrine: Dose Equivalence for Potential Treatment of Anaphylaxis," J. Allergy Clin. Immunol., 117:398-403 (2006).
Rawas-Qalaji et al., "Fast-Disintegrating Sublingual Epinephrine Tablets: Effect of Epinephrine Load on Tablet Characteristics," AAPS PharmSciTech, 7:E1-E7 (2006).
Rawas-Qalaji et al., "Fast-Disintegrating Sublingual Epinephrine Tablets: Long Team Stability Study," AAPS 7(52) Abstract W5219 (2005).
Rawas-Qalaji et al., "Formulation of Fast-Disintegrating Sublingual Epinephrine Tablets for the First-Aid Treatment of Anaphylaxis Away from Health Care Facilities," AAPS 6(4) Abstract W4178(2004).
Rawas-Qalaji et al., "Evaluation of the Effect of Changing Tablet Dimensions on the Characteristics of Fast-Disintegrating Sublingual Epinephrine Tablets for the First-Aid Treatment of Anaphylaxis Away from Health Care Facilities," AAPS 6(4) Abstract W4179(2004).
Rawas-Qalaji et al., "Epinephrine for the Treatment of Anaphylaxis: Do All 40 mg Sublingual Epinephrine Tablet Formulations with Similar in Vitro Characteristics Have the Same Bioavailability?" Biopharm. Drug Dispos., 27:427-435 (2006).
Rawas-Qalaji et al., "Development of Epinephrine Nanoparticles Using Chitosan for the Treatment of Anaphylaxis," Poster Presentation at the 2011 AAPS Annual Meeting and Exposition, Oct. 23-27, 2011, Washington DC, Poster No. W4174.
Sastry et al., "Drug Delivery to the Oral Cavity: Molecule to Market," Chapter 13, pp. 311-316 (2005), Taylor & Francis, CRC Press.
Sastry et al., "Recent Technological Advances in Oral Drug Delivery—A Review," Pharm. Sci. Technol. Today, 3:138-145 (2000).
Saxena, "Sublingual Versus Vaginal Route of Misoprostol for Cervical Ripening Prior to Surgical Termination of First Trimester Abortions," Eur. J. Odst. Gynecol. Reprod. Biol., 125:19-113, (2006).

(56) References Cited

OTHER PUBLICATIONS

Scavone et al., "The Pharmacokinetics and Pharmacodynamics of Sublingual and Oral Alprazolam in the Post-Prandial State," Eur. J. Clin. Pharmacol., 42:439-443 (1992).
Schiermeier et al., "Fast Disposable Ibuprophen Tablets," Eur. J. Pharm. Sci., 15:295-305 (2002).
Sharma et al., "Manufacturing Technology Choices for Mouth Dissolving Tablets," Pharm. Tech. North America, 10-15 (2003).
Sigma-Aldrich, Material Safety Data Sheet, Version 3.2, printed May 1, 2012.
Simons, "First-Aid Treatment of Anaphylaxis to Food: Focus on Epinephrine," J. Allergy Clin. Immunol., 113:837-844 (2004).
Simons et al., "Sublingual Epinephrine Administration in Humans: A Preliminary Study," J. Allergy Clin. Immunol., 113:S260 (2004).
Simons, "EpiPen Jr Versus EpiPen in Young Children Weighing 15 to 30 kg at Risk for Anaphylaxis," J. Allergy Clin. Immunol., 109:171-175 (2002).
Simons, "Outdated EpiPen and EpiPen Jr Autoinjections: Past Their Prime?" J. Allergy Clin. Immunol., 105:1025-1030 (2000).
Simons, "Anaphylaxis: Recent Advances in Assessment and Treatment," J. Allergy Clin. Immunol., 124(4):625-636 (2009).
Simons, "Anaphylaxis," J. Allergy Clin. Immunol., 125:S161-S181 (2010).
Simons, et al., "Epinephrine and Its Use in Anaphylaxis", Curr. Opin. Clin. Immunol., 10:354-361 (2010).
Spenard et al., "Placebo-Controlled Comparative Study of the Anxiolytic Activity and of the Pharmacokinetics of Oral and Sublingual Lorazepam in Generalized Anxiety," Biopharm. Drug Dispos., 9:457-464 (1988).
Sugimoto et al., "The Preparation of Rapidly Disintegrating Tablets in the Mouth," Pharm. Dev. Technol., 6:487-493 (2001).
Verm et al., "Current Status of Drug Delivery Technologies and Future Directions," Pharm. Technol., 25:1-4 (2001).
Watenabe et al., "New Compressed Tablet Rapidly Disintegating in Saliva in the Mouth Using Crystalline Cellulose and a Disintegrant," Biol. Pharm. Bull., 18:1308-1310 (1995).

\* cited by examiner

FIG. 12
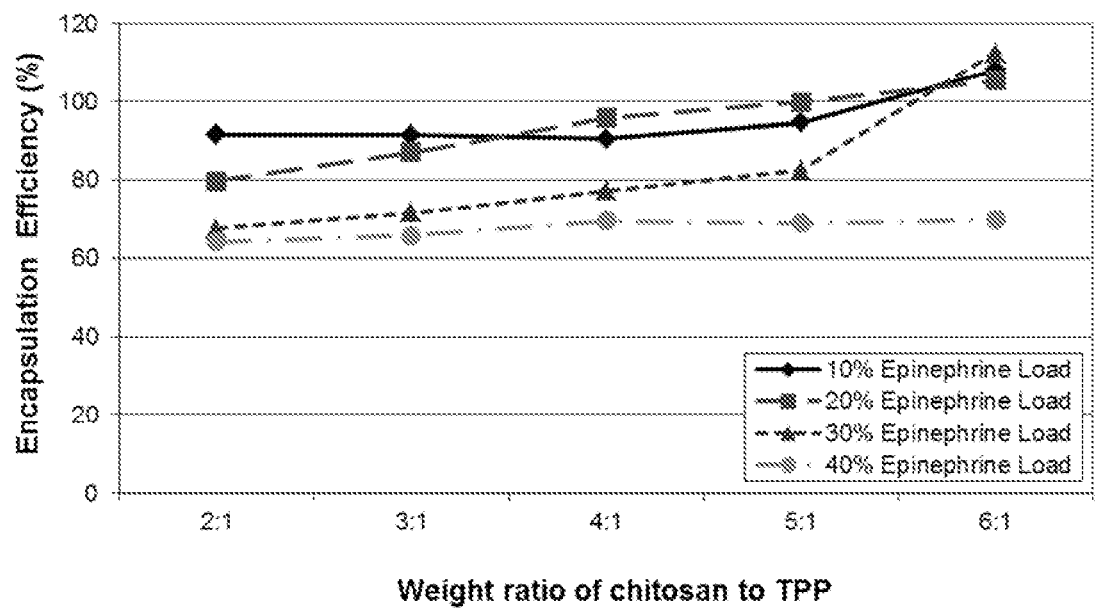
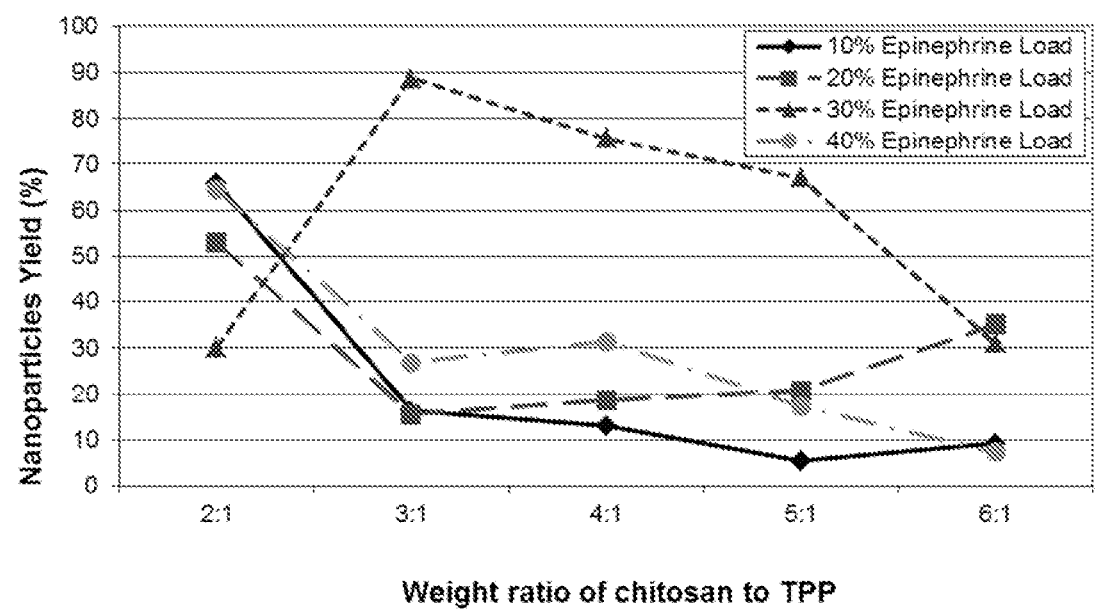
FIG. 13

EPINEPHRINE NANOPARTICLES, METHODS OF FABRICATION THEREOF, AND METHODS FOR USE THEREOF FOR TREATMENT OF CONDITIONS RESPONSIVE TO EPINEPHRINE

CROSS REFERENCE TO RELATED APPLICATIONS

This application is a continuation of U.S. application Ser. No. 14/353,118, filed Apr. 21, 2014; which is a National Stage of International Application No. PCT/US2012/061074, filed Oct. 19, 2012; which claims the benefit of the priority of U.S. Provisional Patent Application No. 61/550,359, filed Oct. 21, 2011; the content of each of which is hereby incorporated by reference in its entirety.

FIELD OF THE INVENTION

The invention generally relates to compositions and methods for treatment of conditions responsive to epinephrine (also known as adrenaline), particularly to compositions and methods for emergency treatment of conditions responsive to epinephrine, and most particularly to compositions including epinephrine nanoparticles for sublingual administration in treatment of conditions responsive to epinephrine.

BACKGROUND

Tablets that disintegrate or dissolve rapidly in the patient's mouth without the use of water are convenient for the elderly, young children, patients with swallowing difficulties, and in situations where water is not available. For these specially designed formulations, the small volume of saliva that is available is sufficient to disintegrate or dissolve a tablet in the oral cavity. The drug released from these tablets can be absorbed partially or entirely into the systemic circulation from the buccal mucosa or sublingual cavity, or can be swallowed as a solution to be absorbed from the gastrointestinal tract.

The sublingual route usually produces a faster onset of action than traditional orally administered tablets and the portion absorbed through the sublingual blood vessels bypasses the hepatic first pass metabolic processes (Birudaraj et al., 2004, *J Pharm Sci* 94; Motwani et al., 1991, *Clin Pharmacokinet* 21: 83-94; Ishikawa et al., 2001, *Chem Pharm Bull* 49: 230-232; Price et al., 1997, *Obstet Gynecol* 89: 340-345; Kroboth et al., 1995, *J Clin Psychopharmacol* 15: 259-262; Cunningham et al., 1994, *J Clin Anesth* 6: 430-433; Scavone et al., 1992, *Eur J Clin Pharmacol* 42: 439-443; Spenard et al., 1988, *Biopharm Drug Dispos* 9: 457-464).

Likewise, due to high buccal and sublingual vascularity, buccally- or sublingually-delivered drugs can gain direct access to the systemic circulation and are not subject to first-pass hepatic metabolism. In addition, therapeutic agents administered via the buccal or sublingual route are not exposed to the acidic environment of the gastrointestinal tract (Mitra et al., 2002, *Encyclopedia of Pharm. Tech.*, 2081-2095). Further, the buccal and sublingual mucosas have low enzymatic activity relative to the nasal and rectal routes. Thus, the potential for drug inactivation due to biochemical degradation is less rapid and extensive than other administration routes (de Varies et al., 1991, *Crit. Rev. Ther. Drug Carr*. Syst. 8: 271-303).

The buccal and sublingual mucosas are also highly accessible, which allows for the use of tablets which are painless, easily administered, easily removed, and easily targeted. Because the oral cavity consists of a pair of buccal mucosa, tablets, such as fast disintegrating tablets, can be applied at various sites either on the same mucosa or, alternatively, on the left or right buccal mucosa (Mitra et al., 2002, Encyclopedia of Pharm. Tech., 2081-2095). In addition, the buccal and sublingual routes could be useful for drug administration to unconscious patients, patients undergoing an anaphylactic attack, or patients who sense the onset of an anaphylactic attack.

Anaphylaxis is a sudden, severe systemic allergic reaction, which can be fatal within minutes. Epinephrine (Epi) is the drug of choice for the treatment of anaphylaxis worldwide (Joint Task Force on Practice Parameters, 2005, *J Allergy Clin Immunol* 115: S483-S523; Lieberman, 2003, *Curr Opin Allergy Clin Immunol* 3: 313-318; Simons, 2004, *J Allergy Clin Immunol* 113: 837-844). It is available as an injectable dosage form in ampoules or in autoinjectors, however these are underused when anaphylaxis occurs (Simons, F. E. R. *J Allergy Clin Immunol* 124(4):625-636 2009; Simons, F. E. R. *J Allergy Clin Immunol* 125:S161-181 2010). The drawbacks of Epi autoinjectors include high cost, perceived large size and bulkiness, limitations on repeated dosing (if required), fear and anxiety associated with the use of needles (especially in children), and dosing errors caused by incorrect techniques of administration (Simons, K. J. et al. *Current Opinion in Clinical Immunology* 10:354-361 2010). Furthermore, in aqueous solutions, epinephrine is unstable in the presence of light, oxygen, heat, and neutral or alkaline pH values (Connors et al., 1986, in *Chemical Stability of Pharmaceuticals: A Handbook for Pharmacists*, Wiley-Interscience Publication: New York).

The sublingual route of administration is a promising alternative route for epinephrine administration. The formulation of sublingual tablets of epinephrine would enable the development of tablets with a range of epinephrine doses to match the population on a mg/kg basis. Sublingual tablets of epinephrine would be easy to carry and self-administer eliminating the fear and anxiety associated with needles used in autoinjectors for young children, as well as readily providing the capability of multiple doses. Feasibility studies in humans and animals have shown that epinephrine can be absorbed sublingually (Gu et al., 2002, *Biopharm Drug Dispos* 23: 213-216; Simons et al., 2004, *J Allergy Clin Immunol* 113: 425-438). The recommended dose of epinephrine for the treatment of anaphylaxis is about 0.01 mg/Kg: usually about 0.2 mL to about 0.5 mL of a 1:1000 dilution of epinephrine in a suitable carrier. Based on historical and anecdotal evidence, an approximately 0.3 mg dose of epinephrine, by subcutaneous (SC) or intramuscular (IM) injection into the deltoid muscle, has been agreed upon as the dose required for the emergency treatment of anaphylaxis. Recent studies have demonstrated that if the approximately 0.3 mg dose is administered IM into the laterus vascularis (thigh) muscle, Epi plasma concentrations are higher and occur more quickly than SC or IM administration into the deltoid muscle. (Joint Task Force on Practice Parameters, 2005, *J Allergy Clin Immunol* 115: S483-S523; Lieberman, 2003, *Curr Opin Allergy Clin Immunol* 3: 313-318; Simons, 2004, *J Allergy Clin Immunol* 113: 837-844)).

As stated above, epinephrine (Epi) is typically administered either subcutaneously (SC) or intramuscularly (IM) by injection. Thus, Epi injections are the accepted first aid means of delivering Epi and are administered either manually or by automatic injectors. It is recommended that persons at risk of anaphylaxis, and persons responsible for children at risk for anaphylaxis, maintain one or more automatic Epi injectors in a convenient place at all times.

Given the difficulties associated with manual subcutaneous (SC) or intramuscular (IM) administration of Epi, such as patient apprehension related to injections or the burden of an at risk person having to always maintain an Epi injector close at hand, there exists a need in the art for more convenient dosage forms which can provide immediate administration of Epi, particularly to a person undergoing anaphylaxis wherein the need for injection or Epi injectors is obviated.

Recently, a novel fast-disintegrating tablet suitable for sublingual (SL) administration was developed. See related U.S. applications: U.S. Provisional Patent Application No. 60/715,180; U.S. Provisional Patent Application No. 60/759,039; U.S. Utility patent application Ser. No. 11/672,503; and U.S. Utility patent application Ser. No. 11/530,360. Sublingual administration of 40 mg epinephrine as the bitartrate salt using these novel tablets resulted in a rate and an extent of epinephrine absorption similar to that achieved following intramuscular injections of 0.3 mg epinephrine in the thigh. Sublingual doses ranging from 5 to 40 mg epinephrine as the bitartrate salt were studied to achieve equivalent plasma concentrations. In an animal model, it was determined that a 40 mg epinephrine dose administered sublingually as a bitartrate salt in tablet form resulted in plasma epinephrine concentrations similar to those achieved by 0.3 mg epinephrine intramuscular (IM) injection (Rawas-Qalaji et al. *J Allergy Clin Immunol* 117:398-403 2006).

Without being bound by theory, it is thought that fabrication of epinephrine into nanoparticles and incorporation of the nanoparticles into a tablet formulation with pharmaceutically-acceptable carriers, penetration enhancers, and mucoadhesives will significantly increase the absorption of SL-administered epinephrine and will result in the reduction of SL epinephrine dose required.

SUMMARY OF THE INVENTION

Epinephrine (Epi) is life-saving in the treatment of anaphylaxis. In community settings, a first-aid dose of epinephrine in an amount of 0.15 mg or 0.3 mg is injected into the mid-outer thigh by patients or caregivers using an auto-injector such as an EpiPen® (epinephrine auto-injector 0.3/0.15 mg, Dey Pharma, L. P. Nappa, Calif.). Epi auto-injectors are under-used because of needle phobia, bulky size, and high cost; additionally, there are only two fixed doses, shelf-life is only 12-18 months, and unintentional injection and injury sometimes occur.

The instant invention circumvents the aforementioned problems by providing a fast-disintegrating epinephrine tablet formulation for anaphylaxis treatment. Although this formulation was designed with regard to anaphylaxis, it is equally effective and contemplated for use in treatment of any condition responsive to epinephrine such as cardiac events, i.e. cardiac arrest, and breathing difficulties, i.e. asthma, bronchial asthma, bronchitis, emphysema, and respiratory infections.

In a validated rabbit model, this fast-disintegrating epinephrine tablet formulation resulted in plasma epinephrine concentrations similar to those achieved after a 0.3 mg epinephrine intra-muscular injection (Rawas-Qalaji et al. *J Allergy Clin Immunol* 117:398-403 2006). Furthermore, epinephrine was stable in these fast-disintegrating tablets for at least seven years.

In one aspect, the invention provides epinephrine nanoparticles. The epinephrine can be either an epinephrine base or an epinephrine bitartrate salt.

The invention also provides stabilized epinephrine nanoparticles.

In another aspect, the invention provides a composition, including epinephrine nanoparticles, capable of enhancing the sublingual bioavailability of epinephrine for the emergency treatment of anaphylaxis.

The invention additionally provides a method for fabrication of stabilized epinephrine nanoparticles and incorporation of the fabricated nanoparticles into orally-disintegrating and fast-disintegrating tablets. The fabrication method includes combining a pre-determined amount of epinephrine (epinephrine base or epinephrine bitartrate salt) and a solvent in a reaction chamber to form a mixture and exposing the mixture to at least one pass at a pre-determined pressure and a pre-determined temperature. The pre-determined pressure ranges from about 8,000 psi to 30,000 psi. The pre-determined temperature ranges from 8.3 to 43.3° C. The solvent with which the epinephrine is combined can be water with or without sodium metabisulfite, isopropyl alcohol (ISP), methanol, acetonitrile, acetone, hexane, chloroform, dichloromethane (DCM), tetrahydrofuran (THF), ethyl acetate, phosphoric acid, and acetic acid.

As described herein, buccal or sublingual oral disintegrating tablets (ODTs) are distinguished from conventional sublingual tablets, lozenges, or buccal tablets by the ODTs' ability to fully dissolve or disintegrate in less than about one minute in the mouth.

The fabrication method for stabilized epinephrine nanoparticles can also include exposing the mixture of epinephrine and solvent to a second pass at a different pre-determined pressure and a different pre-determined temperature from that of the first pass.

Additionally, nanoparticles fabricated by the method can be lyophilized (freeze-dried) or dried under vacuum.

In another aspect, the invention provides a pharmaceutical composition, including epinephrine nanoparticles, formulated for buccal or sublingual administration.

The invention also provides a pharmaceutical composition, including epinephrine nanoparticles, and a pharmaceutically-acceptable carrier for buccal or sublingual administration.

The phrase "pharmaceutically-acceptable carrier" refers to an inactive and non-toxic substance used in association with an active substance, i.e. epinephrine, especially for aiding in the application of the active substance. Non-limiting examples of pharmaceutically-acceptable carriers are diluents, binders, disintegrants, flavorings, fillers, and lubricants. Pharmaceutically-acceptable carriers can have more than one function, i.e. a filler can also be a disintegrant. Additionally, pharmaceutically-acceptable carriers may also be referred to as non-medicinal ingredients (NMIs).

The invention also provides a pharmaceutical composition, for buccal or sublingual administration, including epinephrine nanoparticles and at least one of a pharmaceutically-acceptable carrier, a penetration enhancer, and a mucoadhesive. The pharmaceutical composition can further include at least one of a taste enhancer and a sweetening agent and mouthfeel enhancer. A non-limiting example of a taste enhancer is citric acid. Citric acid masks the bitter taste of epinephrine. A non-limiting example of a sweetening agent and mouthfeel enhancer is mannitol. The pharmaceutical composition can further include at least one of a filler, a lubricant, and a disintegrant. Non-limiting examples include microcrystalline cellulose (filler), magnesium stearate (lubricant), and hydroxypropyl ethers of cellulose (disintegrant).

Additionally, the invention provides a pharmaceutical composition including epinephrine nanoparticles, in which the bitter taste of the epinephrine is masked by a taste enhancer. A non-limiting example of a taste enhancer is citric acid.

In another aspect, the invention provides a method for enhancing sublingual bioavailability of epinephrine in a subject in need thereof including steps for providing a composition including epinephrine nanoparticles and at least one pharmaceutically-acceptable carrier and administering the composition to the subject. The described fast-disintegrating epinephrine tablets enhance bioavailability of epinephrine by releasing epinephrine within sixty seconds of administration.

In another aspect, the invention provides a method for treating a condition responsive to epinephrine in a subject in need thereof including steps for providing a composition including epinephrine nanoparticles and at least one pharmaceutically-acceptable carrier and administering the composition to the subject. Conditions responsive to epinephrine react to administration of epinephrine. Non-limiting examples of conditions responsive to epinephrine include a cardiac event, i.e. cardiac arrest, or an allergic reaction, i.e. anaphylaxis, asthma, or bronchial asthma.

The phrase "effective amount" refers to the amount of a composition necessary to achieve the composition's intended function.

The phase "therapeutically-effective amount" refers to the amount of a composition required to achieve the desired function, i.e. treatment of the condition responsive to epinephrine.

In another aspect, the invention provides a method for treating a breathing difficulty in a subject in need thereof including steps for providing a composition including epinephrine nanoparticles and at least one pharmaceutically-acceptable carrier and administering the composition to the subject. Breathing difficulties responsive to epinephrine include, but are not limited to, breathing difficulties associated with anaphylaxis, asthma, bronchial asthma, bronchitis, emphysema, and respiratory infections.

The invention additionally provides a method for treatment of an allergic emergency in a subject diagnosed with or suspected of having an allergic emergency including steps for providing a composition including epinephrine nanoparticles and at least one pharmaceutically-acceptable carrier and administering the composition to the subject. Non-limiting examples of allergic emergencies are anaphylaxis, asthma, and bronchial asthma.

In an additional aspect, the invention provides a method for treatment of a cardiac event in a subject diagnosed with or suspected of having a cardiac event including steps for providing a composition including epinephrine nanoparticles and at least one pharmaceutically-acceptable carrier and administering the composition to the subject. A non-limiting example of a cardiac event is cardiac arrest.

In another embodiment, the invention provides epinephrine nanoparticles including chitosan and tripolyphosphate (TPP). The epinephrine can be an epinephrine bitartrate salt.

The invention additionally provides epinephrine nanoparticles encapsulated with chitosan and tripolyphosphate (TPP).

The invention additionally provides a pharmaceutical composition including epinephrine nanoparticles encapsulated with chitosan and tripolyphosphate (TPP).

The invention additionally provides epinephrine nanoparticles including or encapsulated with chitosan, tripolyphosphate (TPP), and a taste enhancer. In one embodiment, the taste enhancer is citric acid. The citric acid masks the bitter taste of epinephrine. The invention additionally encompasses a pharmaceutical composition comprising epinephrine nanoparticles including or encapsulated with chitosan, tripolyphosphate (TPP), and a taste enhancer.

The invention additionally provides epinephrine nanoparticles including or encapsulated with chitosan, tripolyphosphate (TPP), and a sweetening agent and mouthfeel enhancer. In one embodiment, the sweetening agent and mouthfeel enhancer is mannitol. The invention additionally encompasses a pharmaceutical composition comprising epinephrine nanoparticles including or encapsulated with chitosan, tripolyphosphate (TPP), and a sweetening agent and mouthfeel enhancer.

The invention additionally provides epinephrine nanoparticles including or encapsulated with chitosan, tripolyphosphate (TPP), and at least one of a taste enhancer, and a sweetening agent and mouthfeel enhancer. In one embodiment, the taste enhancer is citric acid and the sweetening agent and mouthfeel enhancer is mannitol. The invention additionally encompasses a pharmaceutical composition comprising epinephrine nanoparticles including or encapsulated with chitosan, tripolyphosphate (TPP), and at least one of a taste enhancer, and a sweetening agent and mouthfeel enhancer.

The invention provides a pharmaceutical composition, comprising epinephrine nanoparticles including or encapsulated with chitosan and tripolyphosphate (TPP), capable of enhancing the sublingual bioavailability of epinephrine, particularly in the emergency treatment of anaphylaxis.

Any of the above-disclosed epinephrine nanoparticles, compositions, and pharmaceutical compositions can be formulated for buccal or sublingual administration, particularly those epinephrine nanoparticles, compositions, and pharmaceutical compositions intended for use in emergency treatments.

The invention also provides a method for fabrication of stabilized epinephrine nanoparticles including or encapsulated with chitosan and tripolyphosphate (TPP) and incorporation of the fabricated nanoparticles into orally-disintegrating and fast-disintegrating tablets. The method for fabrication includes preparing a first solution including chitosan, acetic acid, and water; preparing a second solution including tripolyphosphate (TPP) and epinephrine; and adding the second solution to the first solution and mixing the solutions together. The method for fabrication can additionally include steps for adding at least one of a taste enhancer and a sweetening agent and mouthfeel enhancer to the solutions. In one embodiment, the taste enhancer is citric acid and the sweetening agent and mouthfeel enhancer is mannitol.

Also encompassed within the invention are epinephrine nanoparticles produced by the fabrication method and compositions including epinephrine nanoparticles produced by the fabrication method.

The invention also provides a pharmaceutical composition including epinephrine nanoparticles, chitosan, tripolyphosphate (TPP), and at least one of a pharmaceutically-acceptable carrier, penetration enhancers, and mucoadhesives for buccal or sublingual administration.

The invention also provides a pharmaceutical composition comprising epinephrine nanoparticles including chitosan, tripolyphosphate (TPP), and at least one of a taste enhancer and a sweetening agent and mouthfeel enhancer. In one embodiment, the taste enhancer is citric acid and the sweetening agent and mouthfeel enhancer is mannitol.

The invention also provides a pharmaceutical composition including epinephrine nanoparticles, chitosan, tripolyphosphate (TPP), and at least one of a pharmaceutically-acceptable carrier, penetration enhancers, mucoadhesives, taste enhancers, and a sweetening agent and mouthfeel enhancer for buccal or sublingual administration.

The invention also provides a pharmaceutical composition including epinephrine nanoparticles, in which the bitter taste of epinephrine is masked by a taste enhancer. In one embodiment, the taste enhancer is citric acid.

In another aspect, the invention provides a method for enhancing sublingual bioavailability of epinephrine in a subject in need thereof including steps for providing a composition including epinephrine nanoparticles encapsulated with chitosan and tripolyphosphate (TPP) and at least one pharmaceutically-acceptable carrier and administering the composition to the subject. The described fast-disintegrating epinephrine tablets enhance bioavailability of epinephrine by releasing epinephrine within sixty seconds of administration.

In another aspect, the invention provides a method for treating a condition responsive to epinephrine in a subject in need thereof including steps for providing a composition including epinephrine nanoparticles encapsulated with chitosan and tripolyphosphate (TPP) and at least one pharmaceutically-acceptable carrier and administering the composition to the subject. Conditions responsive to epinephrine react to administration of epinephrine. Non-limiting examples of conditions responsive to epinephrine include a cardiac event, i.e. cardiac arrest, or an allergic reaction, i.e. anaphylaxis, asthma, or bronchial asthma.

In another aspect, the invention provides a method for treating a breathing difficulty in a subject in need thereof including steps for providing a composition including epinephrine nanoparticles encapsulated with chitosan and tripolyphosphate (TPP) and at least one pharmaceutically-acceptable carrier and administering the composition to the subject. Breathing difficulties responsive to epinephrine include, but are not limited to, breathing difficulties associated with anaphylaxis, asthma, bronchial asthma, bronchitis, emphysema, and respiratory infections.

The invention additionally provides a method for treatment of an allergic emergency in a subject diagnosed with or suspected of having an allergic emergency including steps for providing a composition including epinephrine nanoparticles encapsulated with chitosan and tripolyphosphate (TPP) and at least one pharmaceutically-acceptable carrier and administering the composition to the subject. Non-limiting examples of allergic emergencies are anaphylaxis, asthma, and bronchial asthma.

In an additional aspect, the invention provides a method for treatment of a cardiac event in a subject diagnosed with or suspected of having a cardiac event including steps for providing a composition including epinephrine nanoparticles encapsulated with chitosan and tripolyphosphate (TPP) and at least one pharmaceutically-acceptable carrier and administering the composition to the subject. A non-limiting example of a cardiac event is cardiac arrest.

In another aspect, any of the above-disclosed epinephrine nanoparticles can be used in the manufacture of any of the above-disclosed compositions and pharmaceutical compositions.

Other objectives and advantages of this invention will become apparent from the following description taken in conjunction with the accompanying drawings, wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

A more complete understanding of the present invention may be obtained by references to the accompanying drawings when considered in conjunction with the subsequent detailed description. The embodiments illustrated in the drawings are intended only to exemplify the invention and should not be construed as limiting the invention to the illustrated embodiments.

FIG. 12 is a graph showing the effect of chitosan to TPP weight ratio and epinephrine load on epinephrine encapsulation efficiency.

FIG. 13 is a graph showing the effect of chitosan to TPP weight ratio and epinephrine load on nanoparticle fabrication yield.

DETAILED DESCRIPTION OF THE INVENTION

For the purpose of promoting an understanding of the principles of the invention, reference will now be made to embodiments illustrated herein and specific language will be used to describe the same. It will nevertheless be understood that no limitation of the scope of the invention is thereby intended. Any alterations and further modification in the described compositions and methods and any further application of the principles of the invention as described herein, are contemplated as would normally occur to one skilled in the art to which the invention relates.

Example 1: One Embodiment of Epinephrine Sublingual Tablet Formulation

Summary of In Vitro Diffusion Experiments and Results

The experiments described herein were carried out to assess the in vitro diffusion of epinephrine nanoparticles. The use of epinephrine nanoparticles instead of epinephrine salt was hypothesized to enhance the sublingual bioavailability of epinephrine from administration of a fast-disintegrating sublingual tablet formulation for the emergency treatment of anaphylaxis and/or treatment of other conditions responsive to epinephrine.

Methods:

The diffusion of 80 µg epinephrine from four formulations, epinephrine base nanoparticles suspension (Epi-NP Susp) (size 200 nm), epinephrine solution (Epi-HBCD Sol); epinephrine base using hydroxypropyl-β-cyclodetrin as a solubilizing agent, epinephrine suspension (Epi-CMC Susp); epinephrine base using 0.3% carboxymethyl cellulose as a suspending agent, and epinephrine bitartrate solution (Epi Bit Sol), was studied over 8.5 hours using automated flow-through Franz cell system (n=6). Cumulative epinephrine concentrations in the receptor cells were measured using HPLC-UV (High Performance Liquid Chromatography system with an ultraviolet detector). The cumulative epinephrine concentration versus time (AUC), maximum epinephrine flux ($J_{max}$), time to reach Jmax ($Jt_{max}$), and epinephrine permeation coefficient (Kp) for each formulation were calculated and statistically analyzed using one-way ANOV and Tukey-Kramer tests, NCSS program, at a level of significance $p<0.05$.

Figure 1:
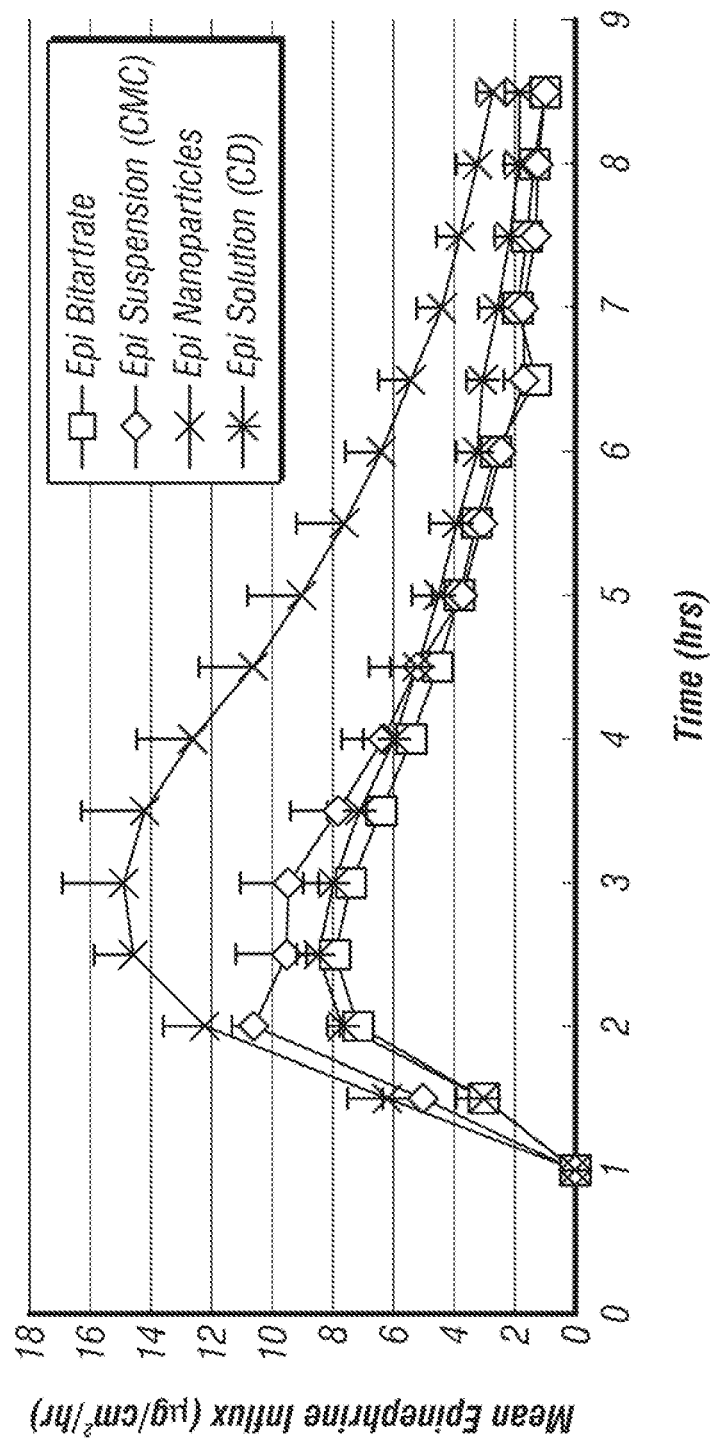
FIG. 1 is a graph showing mean epinephrine influx ($\mu g/cm^2/hr$) obtained from the tested formulations; epinephrine nanoparticles suspension (Epi-NP Susp) (size 200 nm), epinephrine solution (Epi-HBCD Sol), epinephrine suspension (Epi-CMC Susp), and epinephrine bitartrate solution (Epi Bit Sol).

Results:

The AUC and Jmax obtained from epinephrine nanoparticles (Epi-NP Susp), 10.4±1.7 µg/ml/hr and 15.1±1.9 µg/cm$^2$/hr respectively, were significantly higher than epinephrine suspension (Epi-CMC Susp), 5.1±1.1 µg/ml/hr and 10.4±1.6 µg/cm$^2$/hr, epinephrine solution (Epi-HBCD Sol), 5.5±0.5 µg/ml/hr and 8.6±0.3 µg/cm$^2$/hr, and epinephrine bitartrate (Epi Bit Sol), 4.6±0.9 µg/ml/hr and 7.9±1.0 µg/cm$^2$/hr. $Jt_{max}$ was not significantly different between the four formulations. The Kp of epinephrine nanoparticles, 0.19±0.07 cm/hr was significantly higher than epinephrine suspension, 0.13±0.002 cm/hr, epinephrine solution, 0.11±0.04 cm/hr, and epinephrine bitartrate, 0.10±0.04 cm/hr. These results are illustrated in the graph of FIG. 1.

Conclusions:

In these experiments, the permeation of epinephrine nanoparticles (Epi-NP Susp) was almost 2 folds higher than the epinephrine bitartrate (Epi Bit Sol) and epinephrine solution (Epi-HBCD Sol). Epinephrine nanoparticles may have the potential to enhance the sublingual bioavailability of epinephrine compared to epinephrine salt in sublingual tablet formulation. Ex vivo and in vivo studies are contemplated and will be pursued to confirm these results.

Details of Fabrication Experiments and Results

Fabrication of Nanoparticles

Nanoparticles were fabricated from epinephrine base or epinephrine bitartrate (Bit) using high energy fluidization (microfluidization) techniques. These techniques involve the use of an epinephrine suspension of various solvents, particularly water or isopropanol, at various pressures ranging from about 8,000 psi to 30,000 psi for various passes. Particles sizes were measured before and after size reduction using a Mastersizer (Malvern) and/or a NiComp 370 Submicron Particle Sizer (NiComp). The particles were lyophilized (freeze-dried) using a bench top lyophilizer (ART Inc.).

Solubility Studies

In order to determine suitable vehicles to suspend epinephrine base and epinephrine bitartrate (Bit) for nanoparticle fabrication, solubility studies were carried out to select the vehicles that minimally solubilize the drug.

TABLE 1

Solubility

| Sample Name | Amount Dissolved (µg/mL) |
|---|---|
| Epinephrine Base solubility in water | 53.37 |
| Epinephrine Bit solubility in methanol | 209.01 |
| Epinephrine Bit solubility in isopropyl alcohol | 12.30 |
| Epinephrine Bit solubility in acetonitrile | 15.46 |
| Epinephrine Bit solubility in acetone | 31.28 |
| Epinephrine Bit solubility in hexane | 0.53 |
| Epinephrine Bit solubility in choloroform | 1.87 |
| Epinephrine Bit solubility in tetrahydrofuran (THF) | 155.18 |
| Epinephrine Bit solubility in ethyl acetate | 12.60 |

Fabrication of Nanoparticles was First Attempted Using Epinephrine Base

Fabrication: Epinephrine Base

TABLE 2

| | | | | Epinephrine Base | | | |
|---|---|---|---|---|---|---|---|
| Sample | Solvent | Concentration (mg/ml) | Pressure (psi) (#passes) | Particle Size Distribution (nm) (NiComp) | Standard Deviation (SD) | Sample Temperature (° C.) | Sample Color after Processing |
| 1 | water | 0.3 | 30,000 | 273.9 | 179 | 43.3 | brown |
| 2 | water | 0.308 | 29,000 (1) | 334 | 276 | 18.3 | brown |
| 3 | 0.1% phosphoric acid | 1.03 | 15,000 (2) | 335 | 41 | 36.8 first pass 41.1 second pass | brown |
| 4 | 1M acetic Acid | 1.55 | 8,500 (1) 15,000 (1) | 392 | 247 | 36.6 first pass 38.4 second pass | brown |

TABLE 2-continued

Epinephrine Base

| Sample | Solvent | Concentration (mg/ml) | Pressure (psi) (#passes) | Particle Size Distribution (nm) (NiComp) | Standard Deviation (SD) | Sample Temperature (° C.) | Sample Color after Processing |
|---|---|---|---|---|---|---|---|
| 5 | water | 4.03 | 15,000 | 905.9 | 82 | 10 | brown |
| 6 | 0.1 mM sodium metabisulfite in water | 4.02 | 15,000 | 903.1 | 97 | 8.3 | brown |
| 7 | 0.1 mM sodium metabisulfite in 0.1M perchloric acid | 12.02 | 15,000 | 903.1 Note: 111.5 nm (80)% and 2.2 nm (20%) using Zetasizer machine | 326 | 8.3 | pink |

Nanoparticles of epinephrine base in various sizes were produced ranging in diameter from about 273.9 to 905.9 nm.

First Sample

The sample consisted of 30 mg epinephrine in 100 ml of distilled water. One pass at 30,000 psi was applied and a temperature of 43.3° C. was measured after the process. The sample was processed using a M-110P High Energy Fluidizer™ (Microfluidics). The particles were lyophilized using bench top lyophilizer (ART Inc.). The mean particle size obtained was 273.9 nm using the NiComp 370 Submicron Particle Size Analyzer. The sample was stored in the refrigerator.

Second Sample

This sample consisted of 30 mg epinephrine in 100 ml of distilled water. One pass at 29,000 psi was applied and a temperature of 18.3° C. was measured after the process. The homogenizer was setup using the cooling coil. Ice packs and tap water were used to cool the pressurized sample to 14° C. The mean particle size obtained was 334.3 nm using the NiComp 370 Submicron Particle Size Analyzer. The sample was stored in the refrigerator.

Third Sample

This sample was prepared in 0.1% phosphoric acid. The phosphoric acid solution was prepared by diluting 0.5 ml of phosphoric acid 85% (Mallinckrodt Chemicals, LOT H39A04, Exp. Sep. 30, 2011) in 500 ml of distilled water. The epinephrine sample was prepared by weighing 103 mg of epinephrine base into 100 ml of 0.1% phosphoric acid solution prior to sample passes. Two passes at 15,000 psi were applied to the sample. In the first pass a temperature of 36.8° C. was measured after the process and in the second pass a temperature of 41.1° C. was obtained. The mean particle size obtained was 334.6 nm using the NiComp 370 Submicron Particle Size Analyzer. The sample was stored in the refrigerator.

Fourth Sample

This sample was prepared in 1M acetic acid. The 1M acetic acid solution was prepared by diluting 27.5 ml of glacial acetic acid (BDH Aristar, ACS, USP, FCC grade, LOT 200929924) in 500 ml of distilled water. The epinephrine sample was prepared by weighing 155 mg of epinephrine base into 100 ml of 1M acetic acid solution. The M-110p was flushed with distilled water, followed by acetic acid solution prior to sample passes. Two passes were applied to the sample, in the first pass a pressure of 8,500 psi was applied and a temperature of 36.6° C. was measured in the collected sample. In the second pass a pressure of 15,000 psi was applied and a temperature of 38.4° C. was measured in the collected sample. The mean particle size obtained was 392.0 nm using the NiComp 370 Submicron Particle Size Analyzer. The sample was stored in the refrigerator.

Fifth, Sixth, and Seventh Samples

These samples were prepared in a dark room to avoid light. The homogenizer was setup using the cooling coil. Ice packs and tap water were used to cool the pressurized samples. Higher drug concentration was used in the seventh sample since the acidic solvent tends to dissolve more drug than the other previously-used solvents.

Visual Observations

The main problem was discoloration (a brown color formed) due to degradation. All samples were discolored to a pinkish color and then became dark brownish after processing, indicating epinephrine instability. The seventh sample (water+0.1 mM sodium metabisulfite +0.1 M perchloric acid) discolored to a slightly pinkish color. 0.1 mM sodium metabisulfite+0.1 M perchloric acid usually provided optimum stability for epinephrine for several months.

Figure 2A:
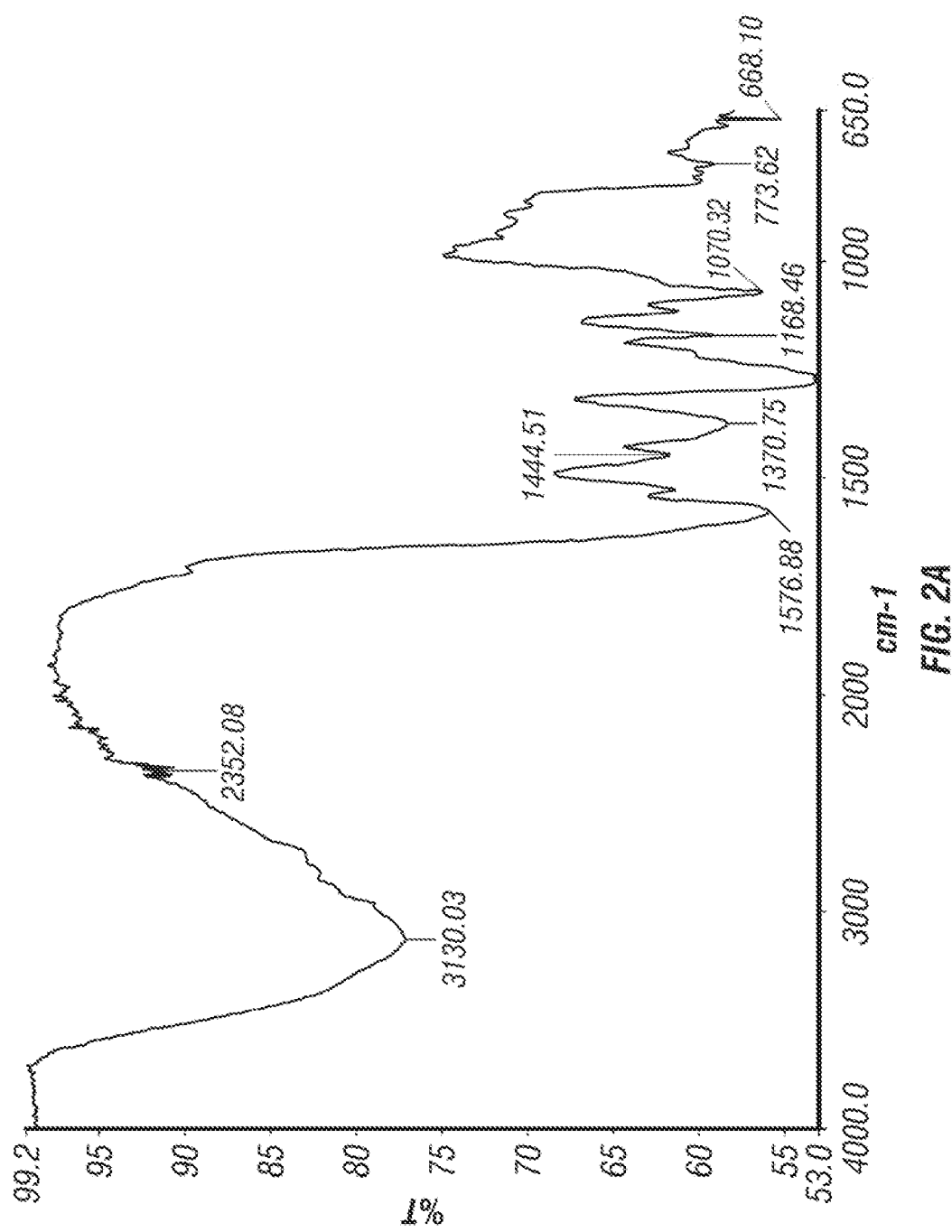
FIG. 2A is a Fourier Transform Infrared (FT-IR) spectrum for epinephrine base nanoparticles after fabrication (processing).
Figure 2B:
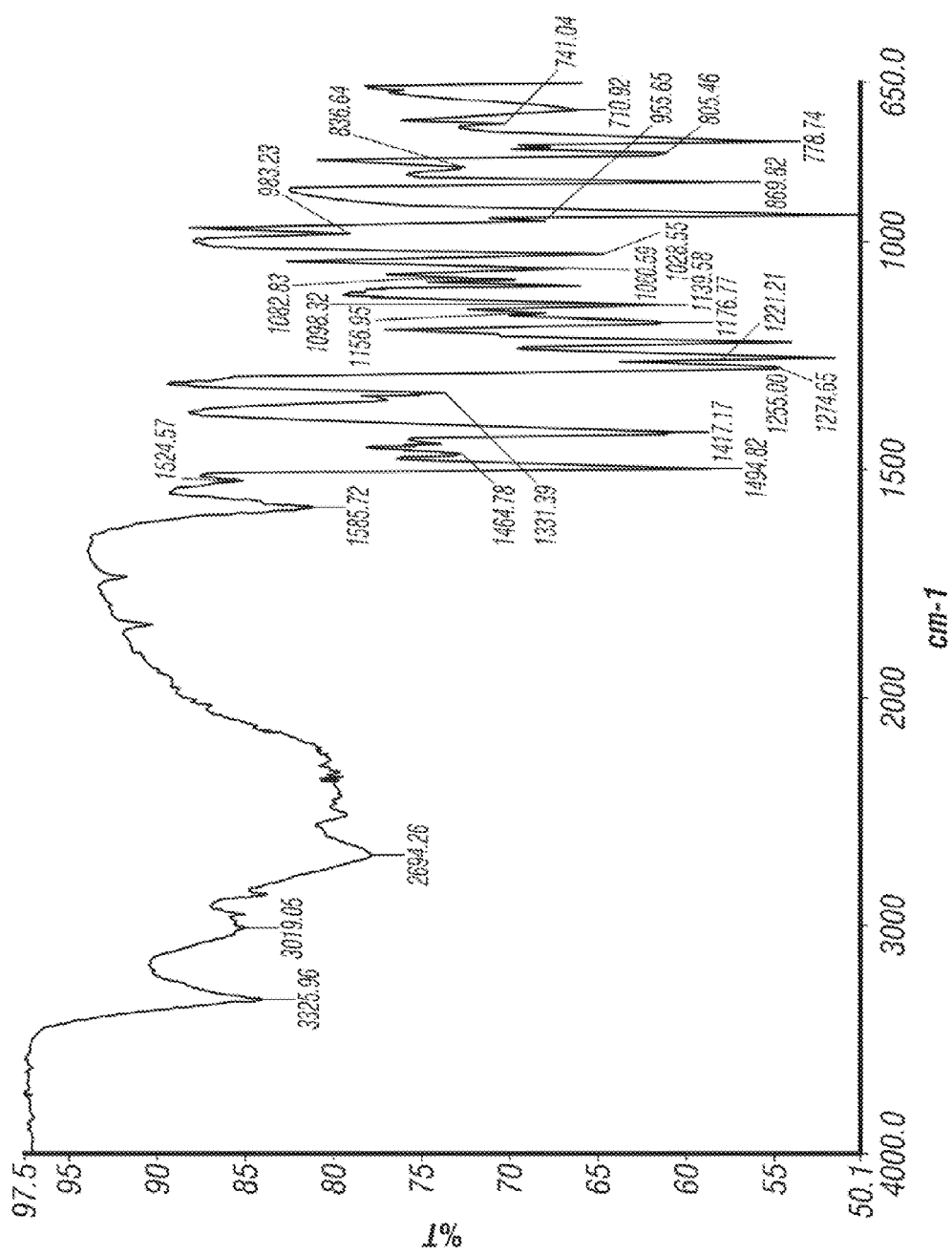
FIG. 2B is a FT-IR spectrum for epinephrine base nanoparticles before processing.

The FT-IR spectrum for epinephrine base before (FIG. 2B) is different from the FT-IR spectrum after processing (FIG. 2A), which reflects the degradation that occurs during processing. The epinephrine base required stabilization with acetic acid or phosphoric acid (in the suspension media) and cooling of the reaction chamber to minimize degradation.

Sizing

The first sample (epinephrine in water) was used.

TABLE 3

Sizes of Epinephrine Base Before and After Processing

| Sample | Before Fabrication (nm) | After Fabrication (110 F., 30 Kpsi) (nm) |
|---|---|---|
| 1 | 33030 | 273.9 |
| 2 | 32530 | |
| 3 | 33160 | |
| Mean | 32900 | |
| Standard Error | 192.04 | |
| Standard Deviation | 332.62 | 179 |

Figure 3:
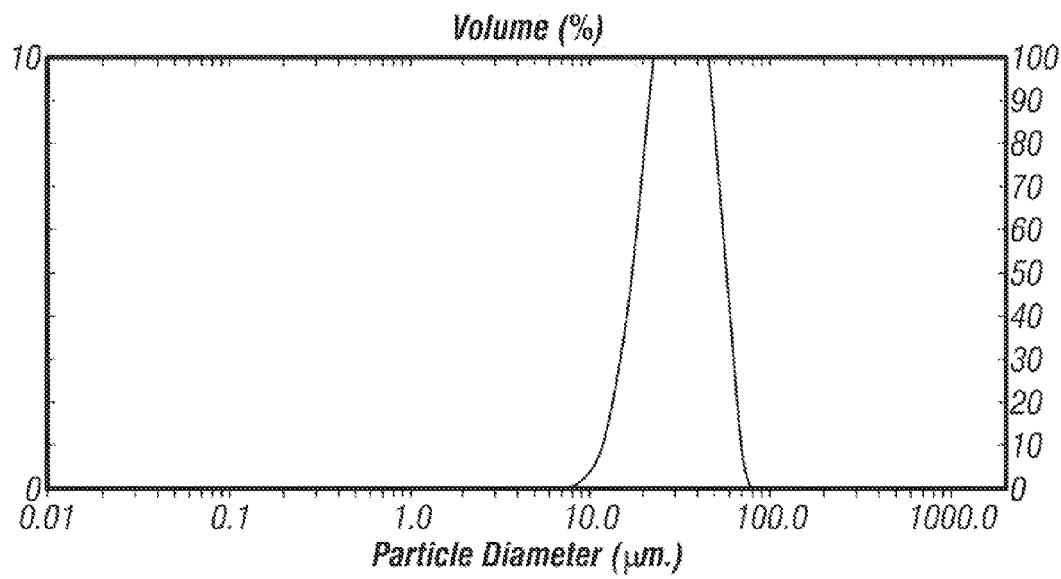
FIG. 3 illustrates particle size distribution of epinephrine base measured before size reduction (processing) using Mastersizer.
Figure 4:
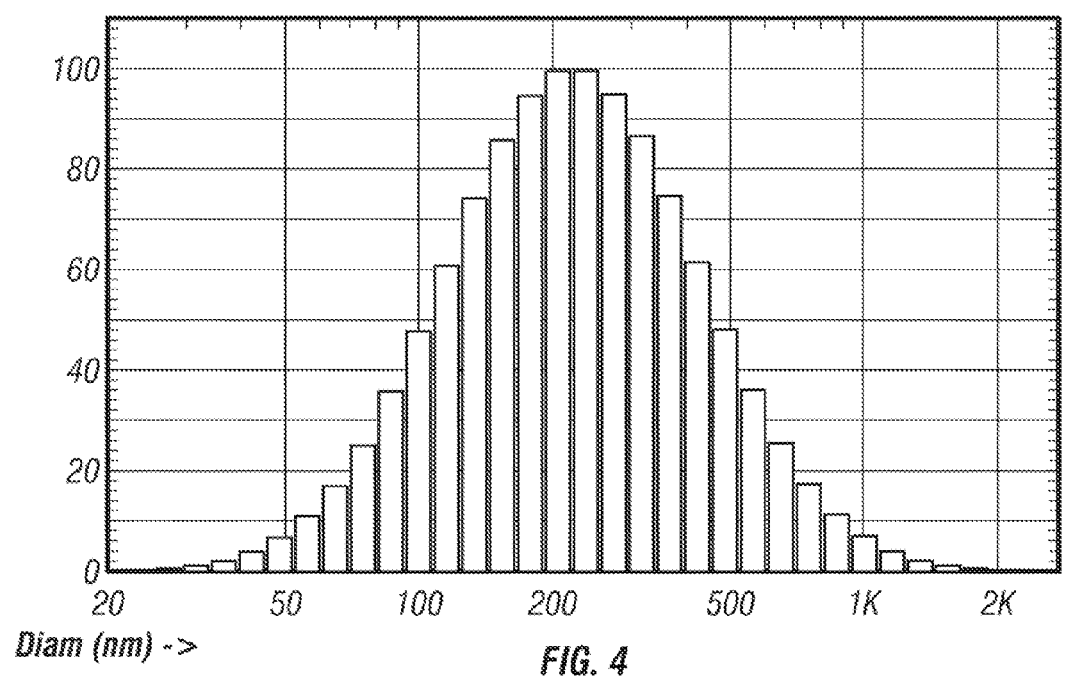
FIG. 4 illustrates particle size distribution of epinephrine base measured after size reduction using NiComp 370.
Figure 5:
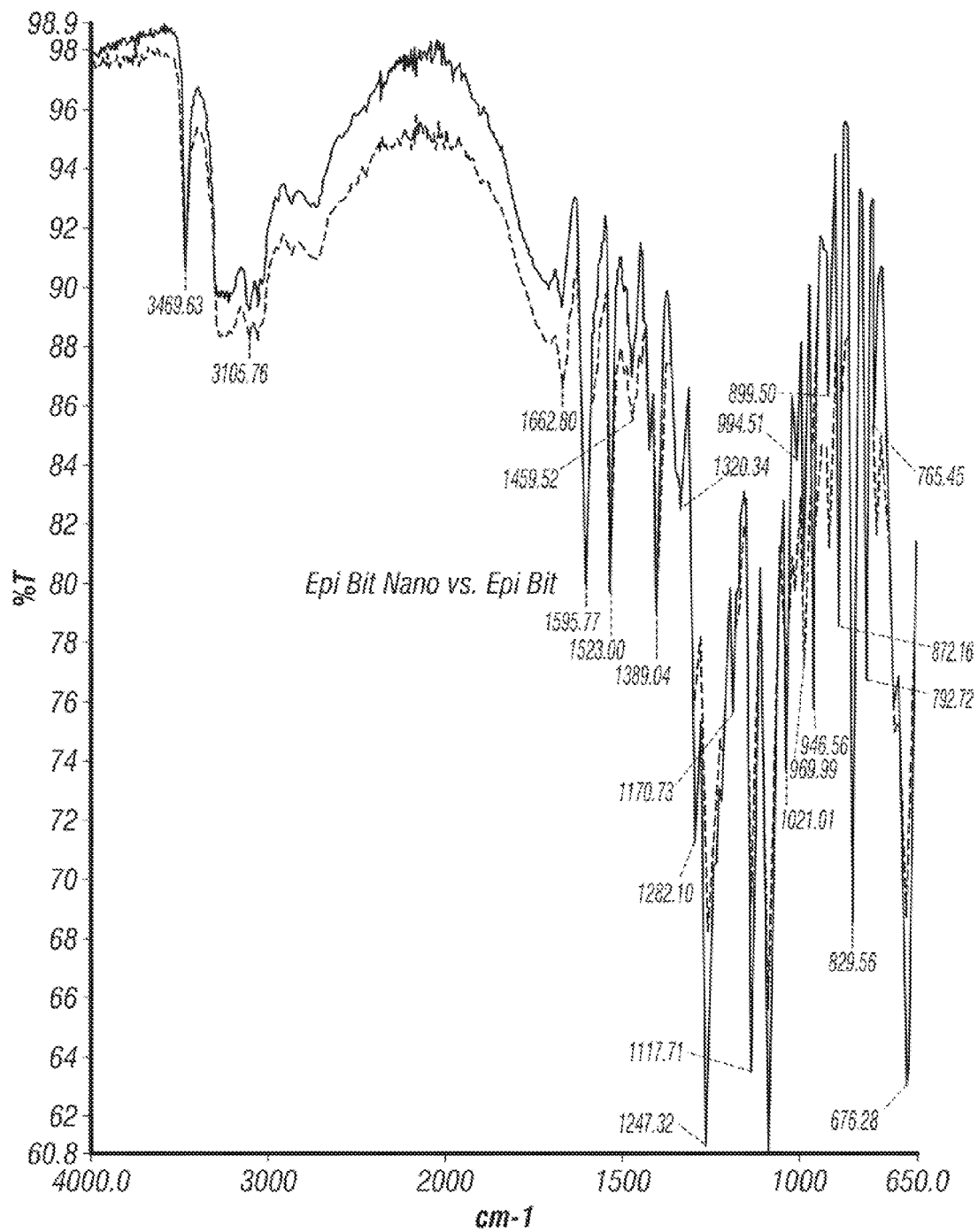
FIG. 5 is a FT-IR spectrum for epinephrine bitartrate nanoparticles before and after processing (nanoparticle fabrication).
Figure 6A:
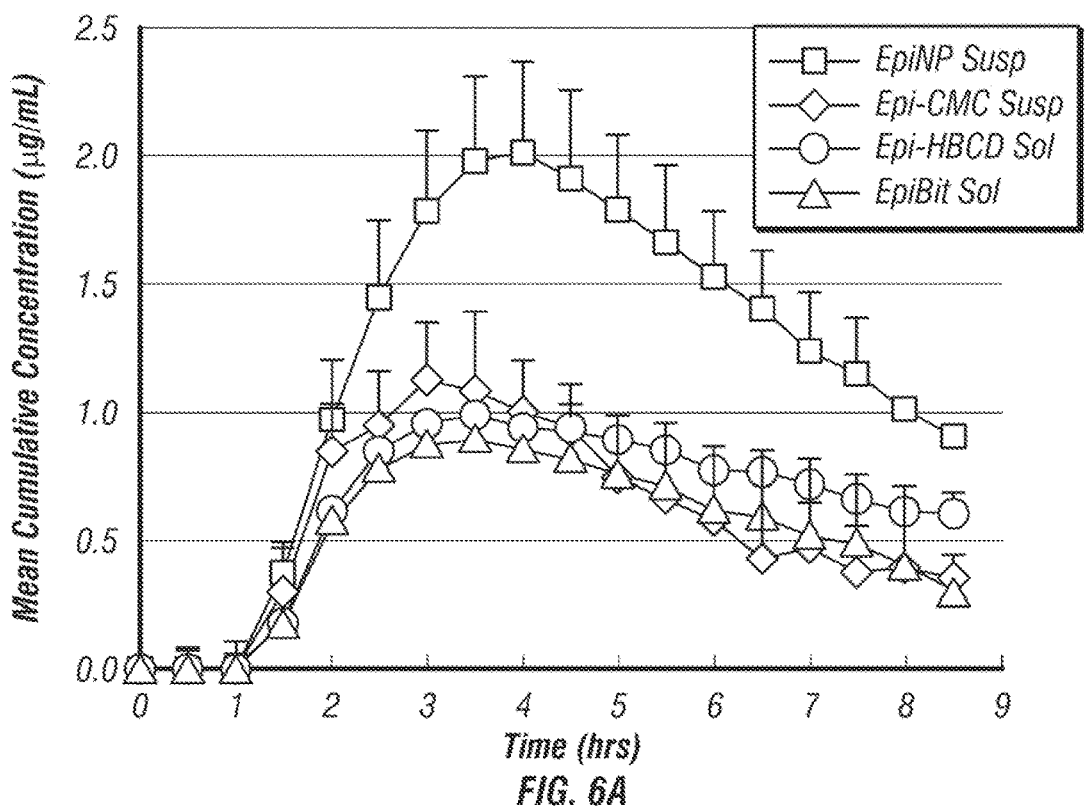
FIG. 6A is a graph showing the AUC (mean cumulative epinephrine concentration) ($\mu g/ml$) obtained from the four tested formulations; Epi-NP Susp, Epi-CMC Susp, Epi-HBCD Sol, and Epi Bit Sol.
Figure 6B:
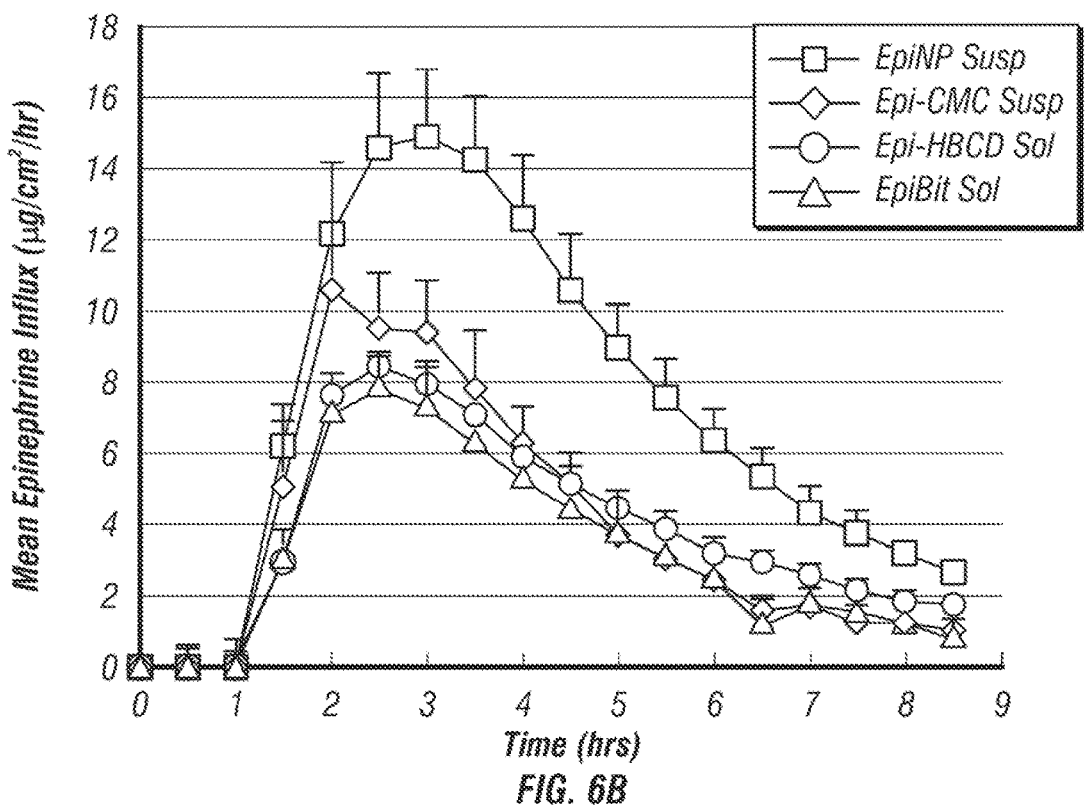
FIG. 6B is a graph showing mean epinephrine influx ($\mu g/cm^2/hr$) obtained from the tested formulations; Epi-NP Susp, Epi-CMC Susp, Epi-HBCD Sol, and Epi Bit Sol.

The epinephrine particle size reduction to nanosize was successful. The mean±SD size was reduced from 32.91±0.33 μm (FIG. 3) to 273.9±179.0 nm (FIG. 4).

Fabrication: Epinephrine Bitartrate (Bit)

In light of the instability associated with the epinephrine base particles, fabrication using the epinephrine salt, epinephrine bitartrate, was pursued.

Isopropyl alcohol (IPO) was selected as a suspending vehicle based on its safety profile and the solubility study previously performed (see above) for several solvents.

TABLE 4

Epinephrine Bitartrate (Bit)

| Sample | Solvent | Concentration (mg/ml) | Pressure (psi) (# passes) | PSD nm (NiComp) | Standard Deviation (SD) |
|---|---|---|---|---|---|
| 1 | IPO | 7.0 | 15,000 (1) | 43,000 | >20,000 |
| 2 | IPO | 3.5 | 25,000 (1) | 8,766 | NA |
|   |     |     | 25,000 (1) | 3,879 |    |
| 3 | IPO | 0.875 | 25,000 (1) | 3,971 | 2032 |
| 4 | IPO | 0.70 | 25,000 (6) | 2,368 | 2065 |
|   |     |     | 25,000 (16) | 1,203 | 924 |

The mean±SD size was reduced from 150,700±5000 nm to 1,203±924 nm.

Observations

Nanoparticles of epinephrine bitartrate in various sizes were produced ranging in diameter from about 43,000 to 1,203 nm.

The first sample, a suspension of 7.0 mg/ml, was used as a stock suspension and was used to prepare the other dilutions. Thus, the passes are additive and each (pass) represents an additional pass to the previous dilution.

After ten passes in the last run, includes samples one, two, three, and the first pass of sample 4, the particle size distribution (PSD) did not change (no effect after ten passes) according to NiComp readings.

The fourth sample was processed six times (6 passes in one step) followed by an additional ten passes (for a total of sixteen passes continuously).

The epinephrine bitartrate (salt form of epinephrine) was more stable than the epinephrine base, did not show any discoloration, and tolerated the fabrication conditions (nano-milling).

First Sample

The particle size distribution (PSD) of epinephrine bitartrate after processing (fabrication) using Zetasizer was 5000 nm (60%) and 500-1000 nm (30-40%). The yield of fabricated epinephrine bitartrate after drying was 68%. The Fourier Transformation Infrared (FT-IR) spectrums are similar in both epinephrine bitartrate before and after processing (FIG. 5).

Details of In Vitro Diffusion Experiments and Results

Epinephrine diffusion was evaluated using an automated, flow through cell system (n=6) under the following parameters:

Flow rate: 50 µl/minute

Donor cell orifice area: 0.2 $cm^2$

Sample volume added to donor cell: 200 µl

Medium in receptor cells: phosphate buffer (pH=5.8)

Membrane: 7 Spectra/Por® dialysis membranes (1000 MWt cutoff).

Epinephrine, base or salt equivalent to 400 µg/ml epinephrine base, in the following four different formulations were used:

1) Epinephrine base nanoparticles suspension (Epi-NP Susp).
2) Epinephrine base suspension using 0.3% carboxymethyl cellulose as a suspending agent (Epi-CMC Susp).
3) Epinephrine base solution using hydroxypropyl-β-cyclodetrin as a solubilizing agent (Epi-HBD Sol).
4) Epinephrine bitartrate solution (Epi Bit Sol).

200 µl from each of the four formulations was spiked into the donor cells. Samples were collected every 30 minutes for 8.5 hours and analyzed by High Performance Liquid Chromatography (HPLC) for epinephrine concentration.

HPLC Analysis

HPLC analysis was performed under the following parameters:

PerkinElmer HPLC system with ultraviolet (UV) detector

Column: Econspher (Alltech), $C_{18}$ 4.6×150 mm, 3 µm

Mobile Phase: USP $26^{th}$ Edition, 2003

Flow Rate: 1 ml/minute

Detection Wavelength: 280 nm

Retention Time: epinephrine 4.8 minutes

Statistical Analysis of Results

Results were statistically analyzed using one-way ANOV and Tukey-Kramer tests, NCSS program, at a level of significance $p<0.05$.

Mean±SD values of cumulative epinephrine concentration versus time (AUC), maximum epinephrine flux (JMax), time to reach JMax (tJMax), and epinephrine permeation coefficient (Kp) for each formulation was calculated.

Results

Mean±SD values of cumulative epinephrine concentration versus time (AUC), maximum epinephrine flux (JMax), and epinephrine permeation coefficient (Kp) obtained from Epi-NP Susp were significantly higher than Epi-CMC Susp, Epi-HBCD Sol, and Epi Bit Sol ($p<0.05$). The time to reach JMax (tJMax) was not significantly different between the four formulations. These results are illustrated in the graphs of FIGS. 6A-B.

TABLE 5

| In Vitro Diffusion Data | | | | |
|---|---|---|---|---|
| Formulation: | Epi-NP Susp | Epi-CMC Susp | Epi-HBCD Sol | Epi Bit Sol |
| AUC (µg/ml/hr) | 10.4 ± 1.7* | 5.1 ± 1.1 | 5.5 ± 0.5 | 4.6 ± 0.9 |
| JMax (µg/$cm^2$/hr) | 15.1 ± 1.9* | 10.4 ± 1.6 | 8.6 ± 0.3 | 7.9 ± 1.0 |
| $t_{Jmax}$ (hr) | 9.41 ± 0.26 | 9.41 ± 0.50 | 10.17 ± 0.10 | 10.12 ± 0.09 |
| Kp (cm/hr) | 0.19 ± 0.07* | 0.13 ± 0.002 | 0.11 ± 0.04 | 0.10 ± 0.04 |

Example 2: Second-Generation Epinephrine Sublingual Tablet Formulations

Summary:

Purpose

In vivo bioavailability of epinephrine (Epi) following sublingual (SL) administration of a 40-mg dose from different first-generation (Gen1) fast-disintegrating tablet formulations is affected by the tablet excipients (Rawas-Qalaji et al. *Biopharm Drug Disposition* 27 (9):427-435 2006). The second-generation (Gen2) SL tablets of Epi were designed to evaluate the effect of grade and proportion of excipients on the in vitro characteristics of the tablets, especially the percentage of Epi released from the tablet (dissolution), which was found to be affected by the tablet excipients in the first-generation tablets (Gen1).

Methods

Epi 40-mg SL tablet formulations (F), Gen1 (F2, F9, and F10), and Gen2 (F1 and F3-8) containing 0-25% mannitol (M), using a single grade or combinations of grades of microcrystalline cellulose (MCC: KG-802, PH-301, PH-M-06), were prepared by direct compression. The effect of adding citric acid for taste-masking was also evaluated. All formulations were evaluated for USP weight variation (WV) and content uniformity (CU). Disintegration times (DT) and dissolution at 60 seconds, expressed as percent of drug released (% DR), were determined using procedures that simulated the SL administration site (AAPS *Pharm Sci Tech* 12:544-552 2011).

Results

All ten formulations were within USP limits for WV and CU. Dissolution times (DT) of all formulations were <20 seconds. Incorporation of up to 15% mannitol (M) into tablet formulations (Gen2, F1, F3, F4, F5, F7) did not affect % DR, but it decreased significantly ($p<0.05$) when M load was increased to 25% (Gen1, F9, F10; and Gen2 F6) and 25% (Gen2,e). At M up to 15%, the incorporation of the MCC grades PH-301 (Gen1, F2; and Gen2, F1, F3, F4, F5, F7) and/or PH-M-06 (Gen1, F9; and Gen2, F1, F4, F5, F7) resulted in higher % DR compared to KG-802 (Gen2, F8). Gen2, F7 that contained PH-301 and PH-M-06 at ratio 6:1 and citric acid for taste masking resulted in virtually complete % DR.

Conclusion

Second generation formulations that contain mannitol at 15% as a sweetening agent and to enhance the mouthfeel of the tablet, a combination of two MCC grades (PH-301: PH-M-06) at 6:1, and a citric acid to mask the taste of Epi resulted in SL Epi tablet formulations with optimal DT and % DR.

Introduction:

In a validated animal model, first-generation (Gen1) 40 mg fast-disintegrating Epi tablet formulation and a 0.3 mg Epi from intramuscular (TM) injection resulted in similar Epi plasma concentrations (*J Allergy Clin Immunol* 117:398-403 2006).

For selection of the optimal first-generation (Gen1) formulations for in vivo evaluation in the validated animal model, disintegration time (DT) was used as the primary in vitro procedure. However in previous in vivo and in vitro studies, the sublingual administration of a 40 mg dose from different first-generation (Gen1) fast-disintegrating tablet formulations with similar DTs resulted in different bioavailabilities (Rawas-Qalaji et al. *Biopharm Drug Disposition* 27 (9):427-435 2006). It was noted that the excipients affect the rate and extent of epinephrine dissolution and therefore its bioavailability. Dissolution assessment is a more selective in vitro test that should be used as a potential predictive tool for the in vivo results. Thus, second-generation (Gen2) epinephrine sublingual tablet formulations were developed by evaluating the effect of the grade and proportion of excipients in test formulations on epinephrine dissolution.

The instant inventors developed a unique dissolution apparatus that simulates the conditions in the sublingual cavity (Rachid, O. et al. *AAPS Pharm Sci Tech* 12(2):544-552 2011) and overcomes the problems associated with the use of an official USP dissolution apparatus (USP/NF. *Physical Tests: Dissolution* (711); 22/17 ed. Rockville, Md.: United States Pharmaceutical Convention Inc; 2007) for sublingual tablets. The limited volume of saliva produced over a short period of time in a relatively static environment is the condition in the sublingual cavity that was simulated in the unique dissolution apparatus. It enabled the instant inventors to discriminate among epinephrine sublingual formulations with similar DTs. Using the unique dissolution apparatus, the rate and extent of release of epinephrine was measured to determine the quantity and quality of non-medicinal ingredients (NMIs) that can be added without inhibiting the release and dissolution of epinephrine. Based on these dissolution results, the best performing epinephrine sublingual formulations will be selected for the in vivo studies in the validated animal model to generate in vivo data.

It has been shown using in vitro methods that the quantity and grade of soluble or insoluble NMIs that can be included into the epinephrine sublingual tablet can exert major effects on the tablet characteristics and the rate of drug release (dissolution). These changes affect the rate and extent of epinephrine sublingual absorption. These NMIs include a wide range of grades of insoluble diluents, microcrystalline cellulose (MCC), disintegrates, soluble sweetening and flavoring agents to mask the bitter taste of epinephrine, and secretagogues (agents that promote saliva secretion). The secretagogues can enhance tablet disintegration by promoting saliva excretion which can improve tablet dissolution and epinephrine release, and should promote epinephrine absorption.

Accordingly, the second-generation epinephrine sublingual tablets were formulated with the main objective of the development of the best performing tablet using in vitro studies. The in vitro assessment of the second-generation epinephrine sublingual tablets included the evaluation of weight variation (WV), content uniformity (CU), hardness (H), disintegration time (DT), wetting time (WT), dissolution (percent of drug released, % DR), and taste improvement.

The extent of the bitter taste of epinephrine is unknown raising concern about patient acceptability of a sublingual tablet of epinephrine, especially by children. An electronic tongue (e-tongue) was utilized to assess and predict the bitterness intensity of epinephrine on a bitterness scale. Furthermore, the effect of NMIs, such as sweeteners (e.g. aspartame and acesulfame potassium) and flavors (e.g. citric acid) on the overall taste of the epinephrine sublingual tablets was evaluated and the masking benefit of these NMIs on the bitter taste of epinephrine was measured (Rachid, O. et al. *AAPS Pharm Sci Tech* 11(2):550-557 2010).

Based on the results from the e-tongue and using the unique dissolution assembly, the best performing second-generation epinephrine sublingual tablet formulations were selected for the new series of in vivo bioavailability studies using the validated animal model (Rawas-Qalaji et al. *Biopharm Drug Disposition* 27 (9):427-435 2006). All of the changes in the second-generation epinephrine sublingual formulations that demonstrated improved epinephrine dissolution from in vitro results will be confirmed in vivo using the validated rabbit model to study the epinephrine bioavailability after sublingual absorption.

Hypothesis for Second-Generation Formulation Study:

the second-generation epinephrine sublingual tablets that showed >98% release of medication within 60 seconds (dissolution) will demonstrate both increased rate and extent of epinephrine absorption in the validated animal model after sublingual administration as compared to the first-generation formulations.

Methods:

The optimal first-generation 40 mg epinephrine formulation, tested in the validated animal model (Rawas-Qalaji et al. *Biopharm Drug Disposition* 27 (9):427-435 2006) was used as the model sublingual formulation since it resulted in epinephrine serum concentrations not significantly ($p<0.05$) different from those obtained from a 0.3 mg epinephrine autoinjector.

The effects of varying concentrations of mannitol, and various grades and percentages of microcrystalline cellulose diluents on dissolution (percent of epinephrine dose released and dissolved in 60 seconds) were studied using the novel dissolution apparatus (Rachid, O. et al. *AAPS Pharm Sci Tech* 12(2):544-552 2011).

The effect of the addition of citric acid on masking the bitter taste of epinephrine was evaluated using the electronic tongue (Rachid, O. et al. *AAPS Pharm Sci Tech* 11(2):550-557 2010).

The effect of increasing the weight and dimensions of the sublingual epinephrine tablet formulation to increase the surface area and improve dissolution was also evaluated using the novel dissolution apparatus (Rachid, O. et al. *AAPS Pharm Sci Tech* 12(2):544-552 2011).

The in vitro re-assessment of the first-generation and assessment of the second-generation epinephrine sublingual tablets included the evaluation of weight variation (WV), content uniformity (CU), hardness (H), disintegration (DT), wetting times (WT), dissolution (percent of drug released, % DR), using the novel dissolution apparatus (Rachid, O. et al. *AAPS Pharm Sci Tech* 12(2):544-552 2011), and taste-masking (Rachid, O. et al. *AAPS Pharm Sci Tech* 11(2):550-557 2010) during the development of these tablets.

Figure 7:
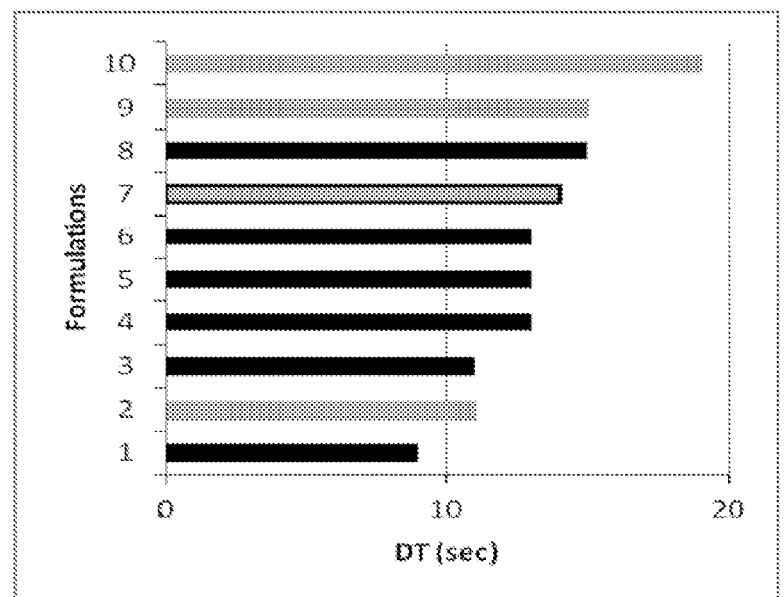
FIG. 7 is a graph showing Disintegration Time (DT) per second of ten different epinephrine 40 mg sublingual tablet formulations.
Figure 8:
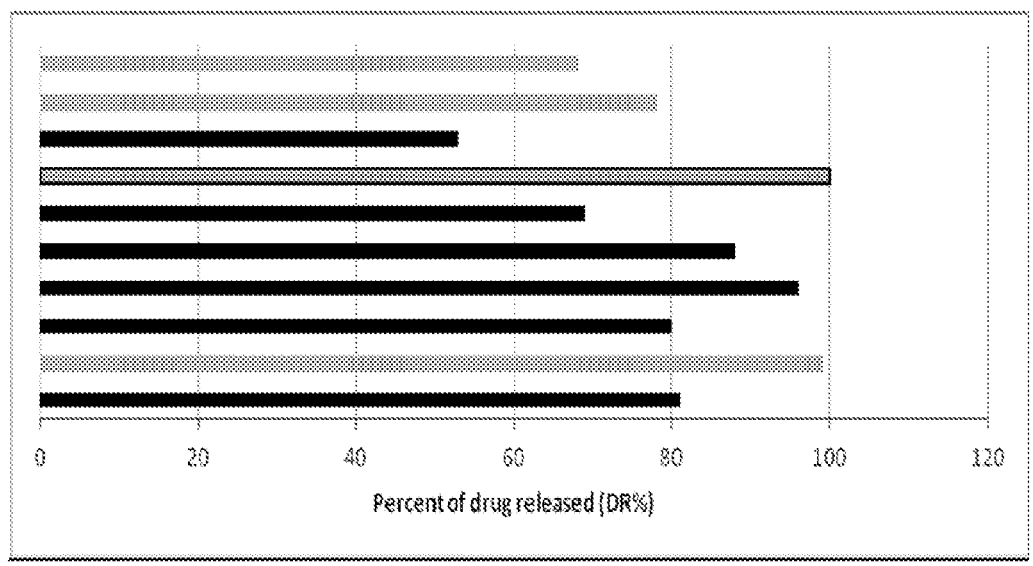
FIG. 8 is a graph showing Percent of Drug Released (DR %) of ten different epinephrine 40 mg sublingual tablet formulations.

Results and Discussion:

Of the numerous first and second generation 40 mg epinephrine sublingual tablets formulated and tested, the results of the ten best prospects were selected based on in vitro test results as reported in Tables 6A-D and Table 7 and FIGS. 7 and 8.

TABLE 6A

Formulation Contents:

| Forumulation | 1 | 2 | 3 | 4 | 5 | 6 | 7 | 8 | 9 | 10 |
|---|---|---|---|---|---|---|---|---|---|---|
| Epinephrine bitartrate (mg) | 72.77 | 72.77 | 72.77 | 72.77 | 72.77 | 72.77 | 72.77 | 72.77 | 72.77 | 72.77 |
| MCC PH-301 (mg) | 74.48 | 66.81 | 46.56 | | 40.83 | 33.06 | 66.80 | | | |
| MCC PH-M-06 (mg) | 11.17 | | | 46.56 | 40.83 | | 11.17 | | 33.06 | |
| MCC KG-802 (mg) | | | | | | | | 53.31 | | |
| Pharmaburst (mg) | | | | | | | | | | 74.23 |
| Mannitol Pearlitol 400DC (mg)/(%) | | | 22.50 (15%) | 22.50 (15%) | 30.00 (15%) | 37.50 (25%) | | 15.00 (10%) | 37.50 (25%) | |
| Mannitol Ludiflash (mg)/(%) | 25.57 (11%) | | | | | | 34.10 (15%) | | | |
| Citric Acid (mg) | 2.50 | | | | 2.50 | | 2.50 | | | |
| L-HPC LH-11 (mg) | 9.51 | 7.42 | 5.17 | 5.17 | 9.07 | 3.67 | 8.66 | 5.92 | 3.67 | |
| Magnesium stearate (mg) | 4.00 | 3.00 | 3.00 | 3.00 | 4.00 | 3.00 | 4.00 | 3.00 | 3.00 | 3.00 |
| Total Tablet Weight (mg) | 200.00 | 150.00 | 150.00 | 150.00 | 200.00 | 150.00 | 200.00 | 150.00 | 150.00 | 150.00 |

TABLE 6B

| Tablet Dimensions | 1 | 2 | 3 | 4 | 5 | 6 | 7 | 8 | 9 | 10 |
|---|---|---|---|---|---|---|---|---|---|---|
| Diameter (mm) | 10.00 | 8.50 | 8.50 | 8.50 | 10.00 | 8.50 | 10.00 | 8.50 | 8.50 | 8.50 |
| Thickness (mm) | 2.00 | 1.75 | 1.75 | 1.75 | 2.00 | 1.75 | 2.00 | 1.75 | 1.75 | 1.75 |

TABLE 6C

| In Vitro Characteristics | 1 | 2 | 3 | 4 | 5 | 6 | 7 | 8 | 9 | 10 |
|---|---|---|---|---|---|---|---|---|---|---|
| Compression Force (kN) | 21.00 | 18.50 | 18.50 | 18.25 | 19.50 | 18.25 | 22-22.5 | 20.50 | 17.75 | 19.25 |
| Hardness (kg) - mean ± SEM | 2.96 ± 0.04 | 1.17 ± 0.04 | 1.23 ± 0.23 | 1.45 ± 0.03 | 2.67 ± 0.08 | 1.23 ± 0.01 | 3.03 ± 0.07 | 1.22 ± 0.02 | 1.23 ± 0.01 | 1.23 ± 0.01 |
| Weight Variation (mg)- mean ± SEM | 201.9 ± 0.64 | 147.22 ± 0.26 | 148.36 ± 0.31 | 148.39 ± 0.2 | 199.4 ± 0.69 | 152.32 ± 0.33 | 202.0 ± 0.81 | 148.64 ± 0.23 | 149.55 ± 0.35 | 149.69 ± 0.46 |
| Content Uniformity (%)- mean ± SEM | 99.04 ± 0.67 | 103.79 ± 0.59 | 99.64 ± 0.78 | 100.08 ± 0.44 | 98.55 ± 0.56 | 100.03 ± 0.48 | 97.82 ± 1.02 | 99.89 ± 0.23 | 98.04 ± 0.4 | 99.88 ± 0.21 |
| Disintegration Time (sec)- mean ± SEM | 9.17 ± 0.31 | 10.67 ± 0.42 | 10.5 ± 0.22 | 12.67 ± 0.21 | 13 ± 0.55 | 13.17 ± 0.31 | 13.5 ± 0.76 | 14.83 ± 0.4 | 15.33 ± 0.33 | 18.5 ± 0.34 |

TABLE 6C-continued

| In Vitro Characteristics | 1 | 2 | 3 | 4 | 5 | 6 | 7 | 8 | 9 | 10 |
|---|---|---|---|---|---|---|---|---|---|---|
| Percent of Drug Released at 60 Sec (%)- mean ± SEM | 80.63 ± 2.42 | 98.66 ± 2.38 | 79.77 ± 1.58 | 96.41 ± 0.75 | 88.39 ± 2.15 | 68.65 ± 1.08 | 99.8 ± 0.41 | 53.46 ± 2.29 | 77.59 ± 2.16 | 67.54 ± 1.59 |

SEM: Standard Error of Mean

TABLE 6D

| In Vivo Characteristics | 1 | 2 | 3 | 4 | 5 | 6 | 7 | 8 | 9 | 10 |
|---|---|---|---|---|---|---|---|---|---|---|
| Area under the Curve, AUC 0-3 h (ng/mL/min)- mean ± SEM | 1861 ± 537 | | | | | | | | 615 ± 87 | 646 ± 202 |
| Cmax (ng/mL)- mean ± SEM | 31 ± 13 | | | | | | | | 6 ± 0.9 | 6.7 ± 3.2 |
| Tmax (min)- mean ± SEM | 9 ± 2 | | | | | | | | 28 ± 10 | 16 ± 4 |

Table 7 shows disintegration time (DT) versus Percent of Drug Released (DR %) at 60 seconds of ten different epinephrine 40 mg sublingual tablet formulations.

TABLE 7

| Formulations | DT (9-19 sec) | % DR at 60 sec (53-100%) |
|---|---|---|
| 1 | 9 | 81 |
| 2 | 11 | 99 |
| 3 | 11 | 80 |
| 4 | 13 | 96 |
| 5 | 13 | 88 |
| 6 | 13 | 69 |
| 7 | 14 | 100 |
| 8 | 15 | 53 |
| 9 | 15 | 78 |
| 10 | 19 | 68 |

All tablets met the criteria for hardness (H), weight variation (WV) and content uniformity (CU) and exhibited disintegration times (DT) between 9 and 19 seconds (Table 6C; Table 7; FIG. 7; and FIG. 8).

These results indicate that the in vitro method to test drug release from sublingual tablets using the unique dissolution apparatus was able to discriminate among formulations which showed similar in vitro data, i.e. disintegration time.

Figure 9A:
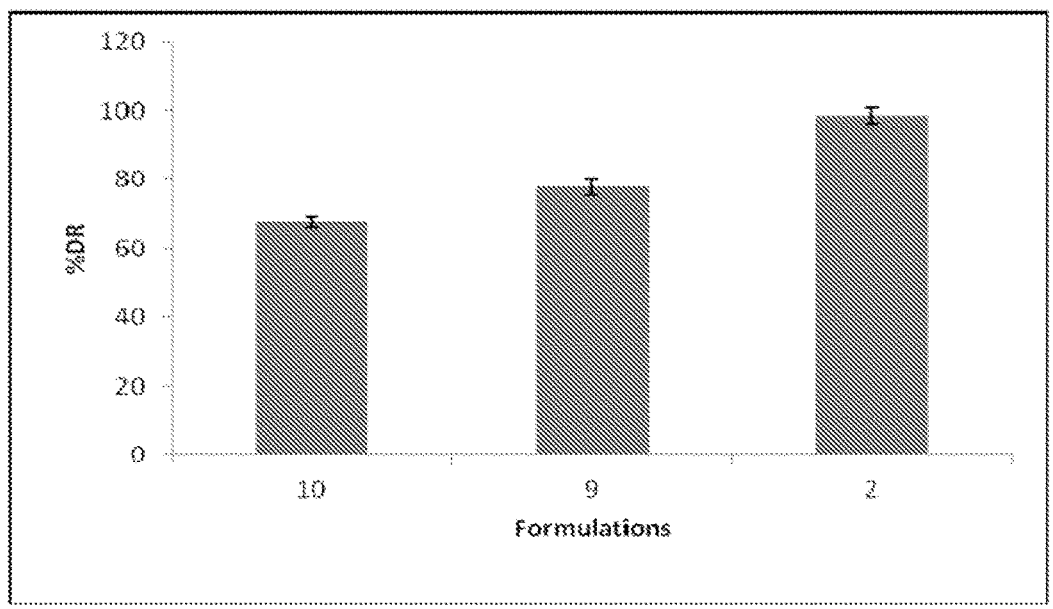
FIG. 9A is a graph showing Percent of Drug Released (DR %) for epinephrine 40 mg sublingual tablet formulations 10, 9, and 2.
Figure 9B:
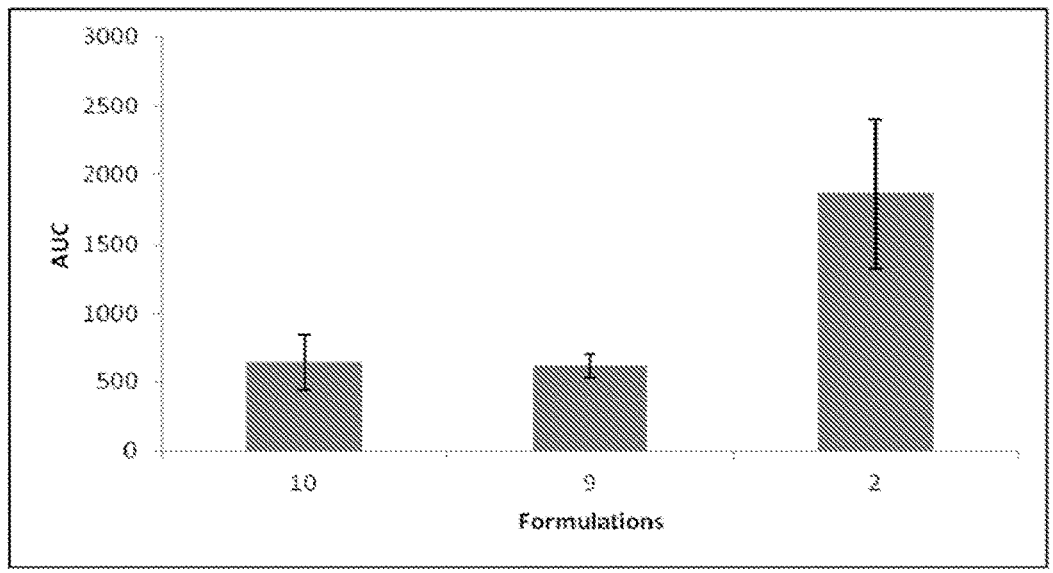
FIG. 9B is a graph showing Area under the Curve (AUC) for epinephrine 40 mg sublingual tablet formulations 10, 9, and 2.

It can be seen from the preliminary data from animal studies that for first-generation formulations 2, 9 and 10, there is some correlation between percent dissolved (% DR), in vitro data, and Area Under the Plasma Concentration versus Time Curve (AUC), in vivo data. This data is reported in Table 8 and FIGS. 9A-B.

TABLE 8

In vitro in vivo Rank Correlations

| Formulation | In vitro DT (sec) | In vitro DR % at 60 sec | SEM | In vivo AUC* | SEM |
|---|---|---|---|---|---|
| 10 | 18.5 | 67.54 | 1.59 | 646 | 202 |
| 9 | 15.33 | 77.59 | 2.16 | 615 | 87 |
| 2 | 10.67 | 98.66 | 2.38 | 1861 | 537 |

*Compared to in vivo AUC of Epipen 0.3 mg (2431 ± 386)

Although first-generation formulations 2, 9, and 10 (see Summary) share similar in vitro disintegration times (DT) of less than 20 seconds, they resulted in widely different bioavailability. In general, disintegration time (DT) is considered to be a poor indicator of in vivo bioavailability. A more predictive in vitro method was required to reflect in vivo behavior. The in vitro drug release method carried out using the unique dissolution apparatus was able to differentiate between these formulations in a rank correlation. The ones that failed in vivo resulted in a DR % of less than 80%. However, the best performing in vivo formulation, formulation 2, resulted in the best DR % of almost 100%.

From the in vitro data (Table 7; FIG. 7; FIG. 8), it can be seen that a second-generation formulation 7 is the optimal formulation. The composition and characteristics of second-generation formulation 7 are shown in Tables 9A-E. The in vivo evaluation of the bioavailability of second-generation formulation 7, using the validated animal model, will be the next study undertaken.

TABLE 9A

The Second Generation of Epinephrine Sublingual Tablets (Formulation 7)

| Tablet Contents | Ingredients | Type | Weight (mg) | Percentage % |
|---|---|---|---|---|
| 1 | Active Ingredient | *epinephrine bitartrate | 72.77 | 36.39 |
| 2 | Filler | **Ceolus, MCC (PH-M-06) | 11.17 | 5.59 |
| 3 | Filler | **Ceolus, MCC (PH-301) | 66.80 | 33.40 |
| 4 | Filler | ***Ludiflash (88% mannitol) | 34.10 | 17.05 |
| 5 | Flavor | †Citric Acid | 2.50 | 1.25 |
| 6 | Disintegrant | ‡L-HPC (LH-11) | 8.66 | 4.33 |
| 7 | Lubricant | Mg Stearate | 4.00 | 2.00 |
| | Tablet Weight | | 200.00 | 100.00 |

*Each tablet contained 72.77 mg Epinephrine bitartrate which is equivalent to 40 mg Epinephrine base.
**Ratio of MCC (PH-301) and MCC (PH-M-06) was kept at 6:1.
***Ludiflash consists of average 88% mannitol, Ludiflash at 17.05% will contain 15% mannitol.
†Ratio of Epinephrine bitartrate and citric acid was kept as 29:1.
‡Ratio of total MCC and L-HPC was kept as 9:1.
MCC (PH-M-06) particle size is 7 μm.
MCC (PH-301) particle size is 50 μm.
Ludiflash particle size is 200 μm.

TABLE 9B

| Tablet Press | |
|---|---|
| Die Size: | 13/32" |
| Die Shape: | Round |
| Punch Surface: | Flat |
| CF (kN): | 22 |

TABLE 9C

Tablet Dimensions

| Diameter: | 10 mm |
|---|---|
| Height: | 2 mm |

TABLE 9D

| Tablet Characteristics | WV (mg) | CU (%) | H (kg) | DT (sec) | DR % (60 sec) |
|---|---|---|---|---|---|
| Mean | 202.00 | 97.82 | 3.03 | 13.50 | 99.80 |
| SD | 2.58 | 3.23 | 0.17 | 1.87 | 1.17 |
| RSD (CV) | 1.28 | 3.30 | 5.61 | 13.86 | 1.18 |
| SEM | 0.97 | 1.02 | 0.07 | 0.76 | 0.41 |

TABLE 9E

Key for Abbreviations Used throughout the Specification

| | |
|---|---|
| MCC: microcrystalline cellulose | DT: disintegration time |
| L-HPC: low-substituted hydroxypropyl cellulose | DR %: percent of drug released |
| | SD: standard deviation |
| WV: weight variation | RSD: relative standard deviation |
| CU: content uniformity | CV: coefficient of variation |
| H: hardness | SEM: standard error of mean |

Improvements in Tablet Formulations (Second Generation compared to First Generation)
1. larger tablet surface area to boost API dissolution and absorption
2. harder tablets to withstand shipping and handling
3. taste enhanced tablets to mask bitter taste of epinephrine
4. improved tablet texture and mouthfeel to enhance patient compliance
5. complete dissolution at 60 seconds Example 3: Epinephrine Sublingual Tablet Formulations Using Chitosan Summary:
Objective:
to prepare epinephrine nanoparticles of optimum size and encapsulation efficiency using chitosan and tripolyphosphate (TPP).
Purpose:
Epinephrine was previously formulated into a fast-disintegrating sublingual tablet (*AAPS Pharm Sci Tech.* 2006; 7(2): Article 41) and the sublingual bioavailability was established in a validated animal model (Rawas-Qalaji et al. *J Allergy Clin Immunol* 117:398-403 2006) for the potential first-aid treatment of anaphylaxis in community settings. The purpose of this study is to develop and characterize epinephrine nanoparticles using chitosan as a polymer to enhance the sublingual bioavailability of epinephrine.
Methods:
Epinephrine bitartrate equivalent to epinephrine 10%, 20%, 30% and 40% were loaded into chitosan nanoparticles from crab shells using ionic gelation method. Chitosan to tripolyphosphate (TPP) weight ratio was studied at 2:1, 3:1, 4:1, 5:1 and 6:1. The medium's pH effect and the reproducibility of the fabrication process were evaluated. Particle size and zeta potential were measured immediately after preparation of nanoparticles using zetasizer (Malvern). All samples were centrifuged at 15000 rpm and the supernatant was analyzed using HPLC-UV to determine the encapsulation efficiency of different weight ratios and epinephrine load. Fabrication yield was calculated from the collected and dried nanoparticles. The mean size, mean zeta potential, encapsulation efficiency, and fabrication yield were plotted against weight ratio of chitosan to TPP for each epinephrine load % and against the evaluated pH levels.
Results:
Nanoparticles in the size range of 50-400 nm were obtained using 2:1 and 3:1 weight ratios of chitosan to TPP. Zeta potential was increased with the increase in weight ratio of chitosan to TPP, and decreased with the increase in epinephrine load %. Encapsulation efficiency was increased by increasing weight ratio of chitosan to TPP; but resulted in lower encapsulation efficiency at 40% theoretical epinephrine load. Epinephrine nanoparticles fabricating at pH 2.75-2.85 resulted in the lowest particles size range. Mean±SD (RSD %) of particle size, zeta potential, epinephrine load, encapsulation efficiency, and fabrication yield for nanoparticles fabricated at 40% theoretical epinephrine load, 2:1 chitosan to TPP weight ratio, and pH of 2.85 were 113±19 nm (17%), 23±2 mV (10%), 28±2% (6%), 69.4% (6%), and 47±4% (9%), respectively.
Conclusion:
By adjusting the chitosan to TPP weight ratio and pH of the medium, optimum and reproducible size of epinephrine nanoparticles can be produced. Encapsulation efficiency of epinephrine into chitosan nanoparticles depends on weight ratio of chitosan to TPP and epinephrine load %.
Introduction:
Epinephrine intramuscular (IM) injection in the thigh is the recommended route of administration for the first aid treatment of anaphylaxis in the community. Due to several drawbacks of the injection alternative methods of administration are being explored.
Examples 2 and 3 disclose fast-disintegrating tablets suitable for sublingual administration. Sublingual administration of 40 mg epinephrine as the bitartrate salt using these tablets resulted in a rate and extent of epinephrine absorption similar to that achieved following intramuscular injection of 0.3 mg epinephrine in the thigh. Sublingual doses ranging from 5 to 40 mg epinephrine as the bitartrate salt were evaluated to achieve equivalent plasma concentrations.
By fabricating epinephrine into nanoparticles and incorporating penetration enhancers and mucoadhesives (if needed) into the tablet formulation, the absorption of sublingually administered epinephrine will significantly increase and will result in the reduction of the sublingual epinephrine dose required.
Chitosan Nanoparticle Fabrication
Epinephrine nanoparticles, 10%, 20%, 30%, and 40%, were fabricated by an ionic gelation method using chitosan and tripolyphosphate (TPP) at weight ratios of 2:1, 3:1, 4:1, 5:1, and 6:1. The effect of the pH of the medium and the reproducibility of the fabrication were also evaluated.
An equivalent amount of epinephrine bitartrate, according to the required theoretical load %, was dissolved in 4 mL deionized water solution containing 3 mg tripolyphosphate (TPP).
Specific amounts of chitosan from crab shells (>75% deacetylated low molecular weight), according to the required ratio, was dissolved in 10 mL acidified deionized water, pH 3 using acetic acid, by vortexing and bath sonication. Undissolved particles were removed by filtration.
The TPP solution containing epinephrine was added dropwise into the chitosan solution under continuous stirring using a magnetic stirrer and was left to stir for approximately 30 minutes.

The formed particles were sized and the zeta potential measured.

Supernatant solution was collected, after centrifugation at 15,000 rpm and 15° C. for approximately 30 minutes, and analyzed for epinephrine content.

The formed pellets, after centrifugation, were washed with deionized water and centrifuged three times at 15,000 rpm and 15° C. for approximately 30 minutes.

The pellets were then suspended with 1 mL deionized water and collected for lyophilization using a bench top lyophilizer (ART Inc.).

The particle size and zeta potential of the suspended nanoparticles were measured right after their fabrication and before centrifugation and freeze drying using Zetasizer NanoZS90 (Malvern).

The same procedure was repeated at pH 2.85, 2.75, and 2.5 for 40% epinephrine theoretical load at 2:1 chitosan to TPP weight ratio to evaluate the effect of medium pH on nanoparticles characteristics.

The pH of 2.85 was then selected to repeat the fabrication procedures three times for 40% epinephrine theoretical load at 2:1 chitosan to TPP weight ratio to evaluate the reproducibility of the fabrication process.

Epinephrine amount encapsulated in the fabricated nanoparticles was calculated indirectly from the epinephrine content in the collected supernatant solution.

Actual drug load (%), encapsulation efficiency (%), and yield (%) were calculated according to the equations:

$$\text{Actual Drug Load}(\%) = \frac{\text{amount of drug in nanoparticles} \times 100}{\text{amount of nanoparticles}}$$

$$\text{Encapsulation Efficiency}(\%) = \frac{\text{actual drug load} \times 100}{\text{theoretical drug load}}$$

$$\text{Nanoparticles Yield}(\%) = \frac{\text{nanoparticles weight} \times 100}{\text{drug weight} + \text{polymer weight}}$$

Epinephrine content in the collected supernatant solution was analyzed using PerkinElmer HPLC system with UV detector and Econspher $C_{18}$, 4.6×150 mm, 3 μm column (Alltech). Analysis and conditions were performed according to USP $26^{th}$ Edition, 2003 "Epinephrine Injection Monograph."

Results

Figure 10:
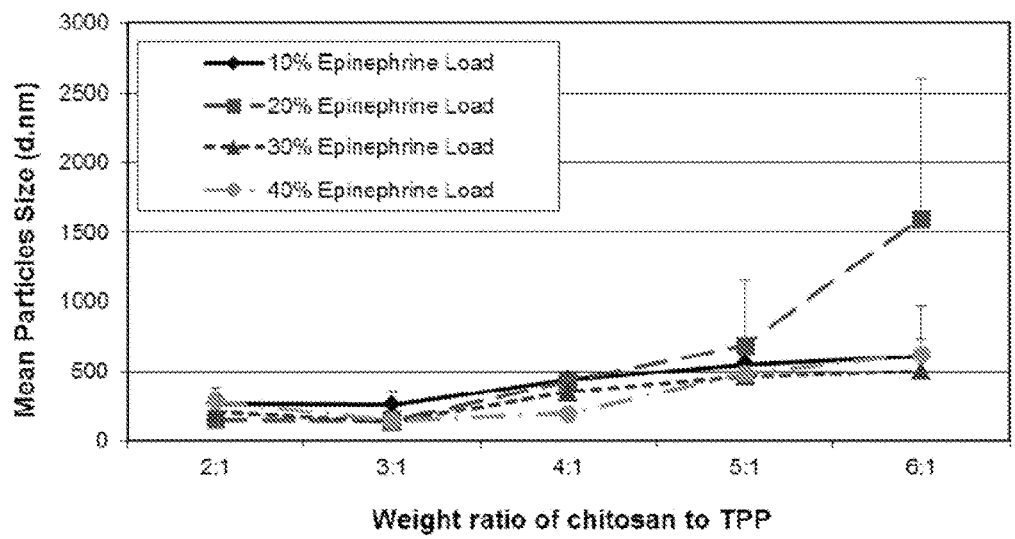
FIG. 10 is a graph showing the effect of chitosan to tripolyphosphate (TPP) weight ratio and epinephrine load on the nanoparticle size.

Chitosan to tripolyphosphate (TPP) weight ratio used in the fabrication of the nanoparticles had a significant impact on the nanoparticle size (FIG. 10). Optimal sizes were obtained at 2:1 and 3:1 weight ratio of chitosan to TPP for the various epinephrine loads (Table 10).

TABLE 10

Mean ± SD particles size of epinephrine nanoparticles

| weight ratio of chitosan to TPP | mean ± SD particle size (dnm) | | | |
|---|---|---|---|---|
| | 10% Epi | 20% Epi | 30% Epi | 40% Epi |
| 2:1 | 273 ± 110 | 155 ± 7 | 209 ± 2 | 289 ± 17 |
| 3:1 | 266 ± 92 | 151 ± 4 | 139 ± 2 | 149 ± 17 |
| 4:1 | 444 ± 17 | 431 ± 64 | 356 ± 37 | 200 ± 4 |
| 5:1 | 550 ± 88 | 685 ± 472 | 469 ± 59 | 487 ± 170 |
| 6:1 | 616 ± 352 | 1596 ± 1013 | 505 ± 228 | 625 ± 20 |

Figure 11:
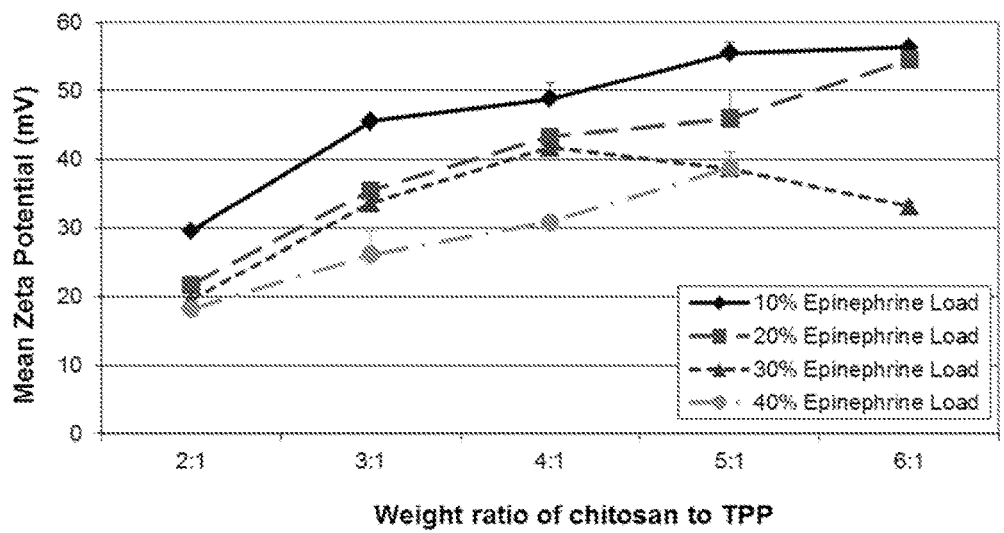
FIG. 11 is a graph showing the effect of chitosan to TPP weight ratio and epinephrine load on the nanoparticle zeta potential.

The zeta potential of the nanoparticles increased with the increase of chitosan to TPP weight ratio and decreased with the increase of epinephrine load (Table 11; FIG. 11).

TABLE 11

Effect of Chitosan to TPP Weight Ratio and Epinephrine Load on the Nanoparticle Zeta Potential

| weight ratio of chitosan to TPP | Mean ± SD Zeta Potential (mV) | | | |
|---|---|---|---|---|
| | 10% Epi | 20% Epi | 30% Epi | 40% Epi |
| 2:1 | 30 ± 02 | 22 ± 11 | 20 ± 19 | 18 ± 08 |
| 3:1 | 44 ± 03 | 26 ± 05 | 34 ± 18 | 26 ± 34 |
| 4:1 | 49 ± 74 | 43 ± 06 | 42 ± 29 | 31 ± 05 |
| 5:1 | 56 ± 16 | 46 ± 11 | 39 ± 24 | 39 ± 09 |
| 6:1 | 56 ± 05 | 55 ± 14 | 33 ± 07 | N/A |

The encapsulation efficiency of epinephrine increased with the increase of chitosan to TPP weight ratio and decreased with the increase of the epinephrine load (Table 12; FIG. 12).

TABLE 12

Effect of Chitosan to TPP Weight Ratio and Epinephrine Load on Epinephrine Encapsulation Efficiency

| weight ratio of chitosan to TPP | Epinephrine Encapsulation Efficiency (%) | | | |
|---|---|---|---|---|
| | 10% Epi | 20% Epi | 30% Epi | 40% Epi |
| 2:1 | 91.6 | 79.8 | 67.5 | 61.0 |
| 3:1 | 91.5 | 87.2 | 71.5 | 65.7 |
| 4:1 | 90.5 | 95.8 | 77.2 | 69.4 |
| 5:1 | 94.7 | 99.9 | 82.5 | 68.9 |
| 6:1 | 108.1 | 105.0 | 112.5 | 69.7 |

The nanoparticle fabrication yield decreased with the increase of the chitosan to TPP weight ratio (Table 13; FIG. 13).

TABLE 13

Effect of Chitosan to TPP Weight Ratio and Epinephrine Load on Nanoparticles Fabrication Yield

| weight ratio of chitosan to TPP | Fabrication Yield (%) | | | |
|---|---|---|---|---|
| | 10% Epi | 20% Epi | 30% Epi | 40% Epi |
| 2:1 | 65.9 | 53.0 | 30.2 | 64.4 |
| 3:1 | 16.4 | 15.7 | 5.8 | 25.9 |
| 4:1 | 13.1 | 18.7 | 75.7 | 31.5 |
| 5:1 | 5.5 | 20.7 | 67 | 17.4 |
| 6:1 | 9.3 | 35.2 | 31.1 | 7.4 |

Figure 14:
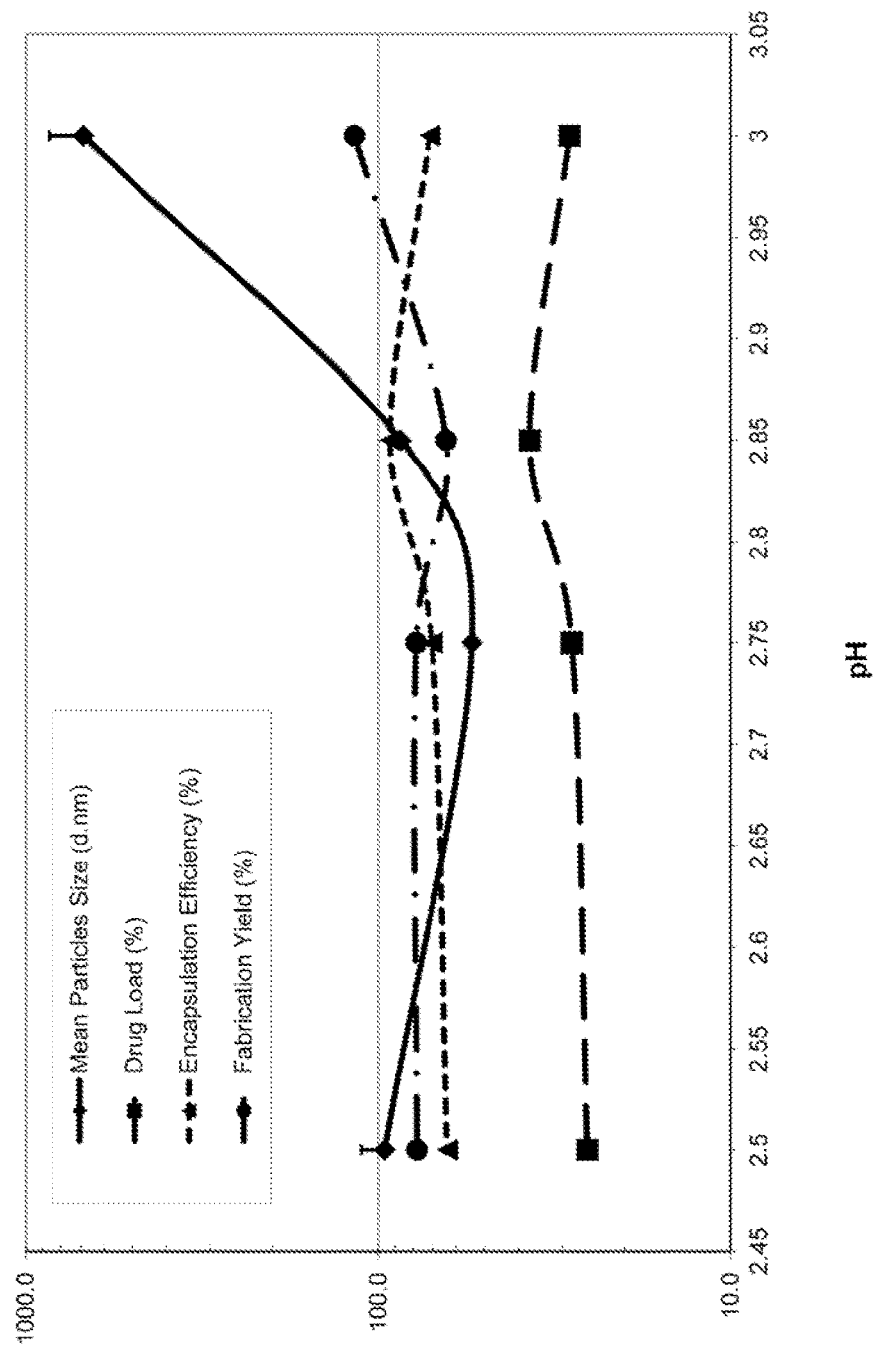
FIG. 14 is a graph showing the effect of the pH of the medium on epinephrine nanoparticle characteristics using 40% Epi theoretical load.

The size of the nanoparticles decreased dramatically with the decrease of the pH of the chitosan solution from 3 to 2.85, 3.75, or 2.5 using 40% epinephrine theoretical loaded (Table 14; FIG. 14).

TABLE 14

Effect of the pH of the Medium on Epinephrine Nanoparticle Characteristics Using 40% Epi Theoretical Load

| pH of chitosan solution | Drug % Load | Encapsulation Efficiency (%) | Fabrication Yeild (%) | Mean ± SD Particle Size (dnm) |
|---|---|---|---|---|
| 3 | 28.7 | 71.5 | 117 | 689 ± 168 |
| 2.85 | 37.2 | 92.8 | 64.1 | 86 ± 0.9 |
| 2.75 | 28.2 | 70.5 | 78.2 | 54 ± 0.4 |
| 2.5 | 25.5 | 63.7 | 77.8 | 96 ± 0.4 |

The nanoparticle fabrication at 40% epinephrine theoretical load and pH 2.85 was reproducible (n=3). The mean±SD and RSD % of particle size, zeta potential, epinephrine load, encapsulation efficiency, and fabrication yield were 113±19 (17%), 23±2 mV (10%), 28±2 (6%), 69±4 (6%), and 47±4 (9%), respectively.

Taken together the data show that optimum size of epinephrine nanoparticles and fabrication yield can be obtained by adjusting the weight ratio of chitosan to TPP. Further, nanoparticles zeta potential and encapsulation efficiency of epinephrine depends on weight ratio of chitosan to TPP and epinephrine load percent (%).

Ultimately, the carefully developed and critically evaluated sublingual epinephrine tablets described herein should have a major impact on the management of life-threatening anaphylaxis, especially in children.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not intended to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The compositions, epinephrine nanoparticles, pharmaceutical tablets, methods, procedures, and techniques described herein are presently representative of the preferred embodiments, are intended to be exemplary and are not intended as limitations on the scope. Changes therein and other uses will occur to those skilled in the art which are encompassed within the spirit of the invention. Although the invention has been described in connection with specific, preferred embodiments, it should be understood that the invention as ultimately claimed should not be unduly limited to such specific embodiments. Indeed various modifications of the described modes for carrying out the invention which are obvious to those skilled in the art are intended to be within the scope of the invention.

What is claimed is:

1. Epinephrine nanoparticles consisting of epinephrine bitartrate, chitosan, and tripolyphosphate; and optionally a taste enhancer.

2. A pharmaceutical composition comprising the epinephrine nanoparticles of claim 1.

3. The composition in accordance with claim 2, further comprising at least one of a pharmaceutically-acceptable carrier, a penetration enhancer, and a mucoadhesive.

4. The composition in accordance with claim 3, furthermore comprising at least one of a taste enhancer and a sweetening agent and mouthfeel enhancer.

5. The composition in accordance with claim 4, wherein the taste enhancer is citric acid and the sweetening agent and mouthfeel enhancer is mannitol.

6. The composition in accordance with claim 4, wherein the composition is formulated for buccal or sublingual administration.

7. A method for enhancing sublingual bioavailability of epinephrine in a subject in need thereof, comprising administering the epinephrine nanoparticles of claim 1 to the subject.

8. A method for treating a condition responsive to epinephrine in a subject in need thereof, comprising administering the epinephrine nanoparticles of claim 1 to the subject.

9. A method for treatment of a breathing difficulty in a subject in need thereof, comprising administering the epinephrine nanoparticles of claim 1 to the subject.

10. A method for treatment of an allergic emergency in a subject diagnosed with or suspected of having an allergic emergency, comprising administering the epinephrine nanoparticles of claim 1 to the subject.

11. A method for treatment of a cardiac event in a subject diagnosed with or suspected of having a cardiac event, comprising administering the epinephrine nanoparticles of claim 1 to the subject.

12. The epinephrine nanoparticles of claim 1, consisting of epinephrine bitartrate, chitosan, and tripolyphosphate.

13. The epinephrine nanoparticles of claim 1, consisting of epinephrine bitartrate, chitosan, tripolyphosphate, and a taste enhancer.

14. The epinephrine nanoparticles of claim 13, wherein the taste enhancer is citric acid.

15. The epinephrine nanoparticles of claim 12, wherein epinephrine bitartrate is encapsulated with chitosan and tripolyphosphate.

16. The epinephrine nanoparticles of claim 1, wherein the weight ratio of chitosan to tripolyphosphate is 2:1, 3:1, 4:1, 5:1, or 6:1.

17. The epinephrine nanoparticles of claim 1, wherein the load of epinephrine is about 10%, about 20% about 30%, or about 40%.

18. The epinephrine nanoparticles of claim 1, having a particle size ranging from 50 to 400 nm.

19. The epinephrine nanoparticles of claim 1, wherein the epinephrine nanoparticles are stabilized epinephrine nanoparticles.

* * * * *